(12) United States Patent
Ries et al.

(10) Patent No.: US 7,155,283 B2
(45) Date of Patent: *Dec. 26, 2006

(54) CONNECTOR HEADER GROMMET FOR AN IMPLANTABLE MEDICAL DEVICE

(75) Inventors: Andrew J. Ries, Lino Lakes, MN (US); Kevin K. Tidemand, East Bethel, MN (US); Jennifer J. Zhao, Plymouth, MN (US); David C. Rice, Blaine, MN (US); Hui Jin, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 454 days.

This patent is subject to a terminal disclaimer.

(21) Appl. No.: 10/732,940

(22) Filed: Dec. 11, 2003

(65) Prior Publication Data

US 2005/0131481 A1   Jun. 16, 2005

(51) Int. Cl.
*A61N 1/00* (2006.01)
(52) U.S. Cl. ....................................................... 607/37
(58) Field of Classification Search .................. 607/36, 607/37
See application file for complete search history.

(56) References Cited

U.S. PATENT DOCUMENTS

| | | | |
|---|---|---|---|
| 3,822,707 A | 7/1974 | Adducci et al. | 128/419 P |
| 4,010,762 A | 3/1977 | Strydom | 131/21 B |
| 4,072,154 A | 2/1978 | Anderson et al. | 128/419 P |
| 4,105,037 A | 8/1978 | Richter et al. | 128/419 P |
| 4,141,752 A | 2/1979 | Shipko | 128/419 P |
| 4,142,532 A | 3/1979 | Ware | 128/419 P |
| 4,154,248 A | 5/1979 | Jones | 128/419 P |
| 4,180,078 A | 12/1979 | Anderson | 128/419 PG |
| 4,182,345 A | 1/1980 | Grose | 128/419 P |
| 4,226,244 A | 10/1980 | Coury et al. | 128/419 P |

(Continued)

OTHER PUBLICATIONS

U.S. Appl. No. 10/732,940, filed Dec. 11, 2003, entitled "Connector Header Grommet for an Implantable Medical Device" to Ries et al.

(Continued)

*Primary Examiner*—Scott M. Getzow
(74) *Attorney, Agent, or Firm*—Daniel G. Chapik; Girma Wolde-Michael

(57) ABSTRACT

Improvements in connector headers of implantable medical devices (IMDs) for making electrical and mechanical connections with a connector element of a proximal connector assembly of an electrical medical lead and components thereof are disclosed. A connector block disposed within a header body of the connector header has a threaded bore aligned with a header grommet aperture and a connector block bore aligned with a header connector bore. A penetrable grommet is disposed within the header grommet aperture, and a setscrew is threaded into the threaded bore having a setscrew socket disposed to be engaged by the tool inserted through the penetrable grommet within the header grommet aperture to enable rotation of the setscrew within the threaded bore to tighten the setscrew against or to loosen the setscrew from a lead connector element received in the header connector bore.

23 Claims, 10 Drawing Sheets

U.S. PATENT DOCUMENTS

| | | |
|---|---|---|
| 4,262,673 A | 4/1981 | Kinney et al. ............ 128/419 P |
| 4,316,471 A | 2/1982 | Shipko et al. ............ 128/419 P |
| 4,445,511 A | 5/1984 | Cowdery et al. ......... 128/419 P |
| 4,461,194 A | 7/1984 | Moore .......................... 81/436 |
| 4,479,489 A | 10/1984 | Tucci ..................... 128/419 P |
| 4,932,409 A | 6/1990 | Hirschberg ............. 128/419 P |
| 5,207,218 A | 5/1993 | Carpentier et al. ... 128/419 PG |
| 5,522,861 A | 6/1996 | Sikorski et al. ................ 607/36 |
| 5,989,077 A | 11/1999 | Mast et al. .................. 439/814 |
| 6,205,358 B1 | 3/2001 | Haeg et al. .................... 607/36 |
| 2001/0034543 A1 | 10/2001 | Haeg et al. .................... 607/36 |
| 2003/0040780 A1 | 2/2003 | Haeg et al. .................... 607/36 |
| 2004/0122481 A1* | 6/2004 | Tidemand et al. ............. 607/37 |

OTHER PUBLICATIONS

U.S. Appl. No. 10/199,601, filed Jul. 19, 2002, entitled "Ultrasonically Welded, Staked or Swaged Components in an Implantable Medical Device" to Haeg et al.

* cited by examiner

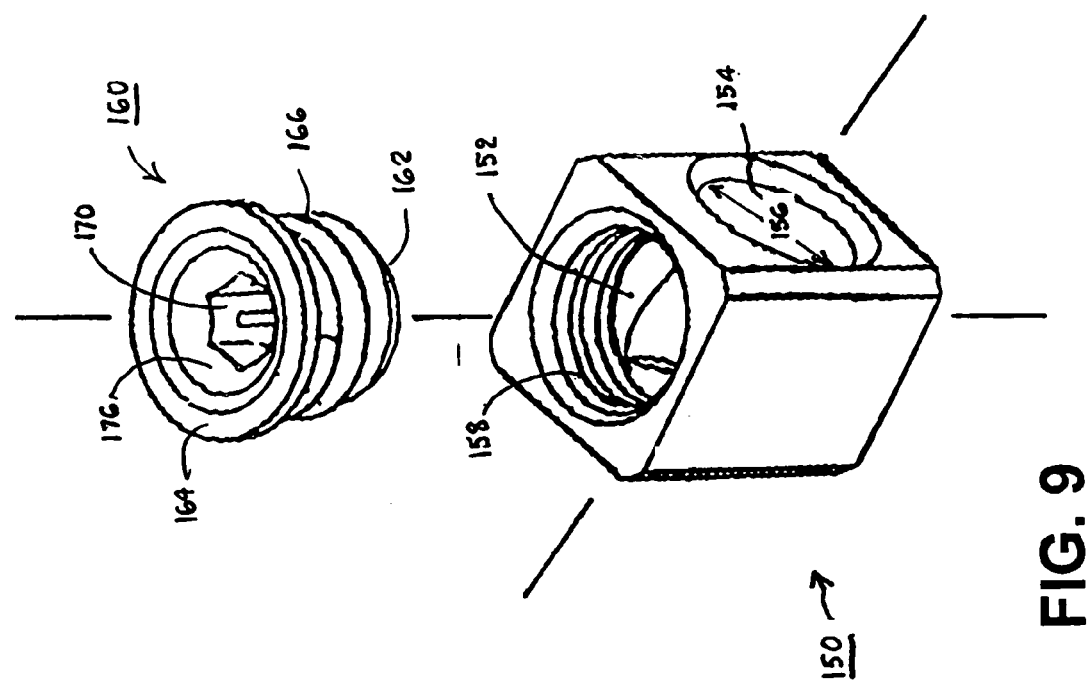
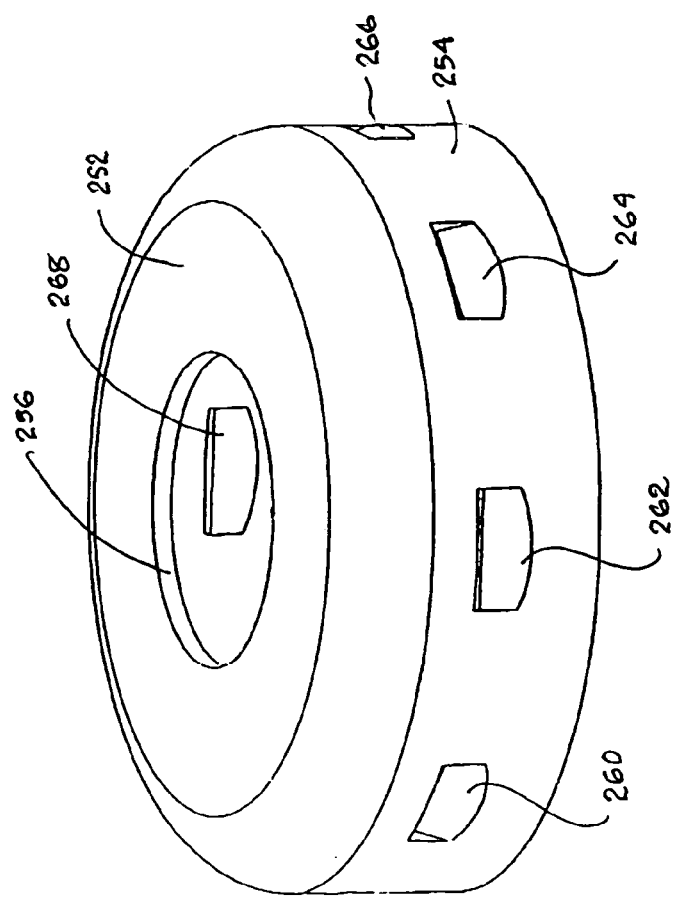

FIG. 16
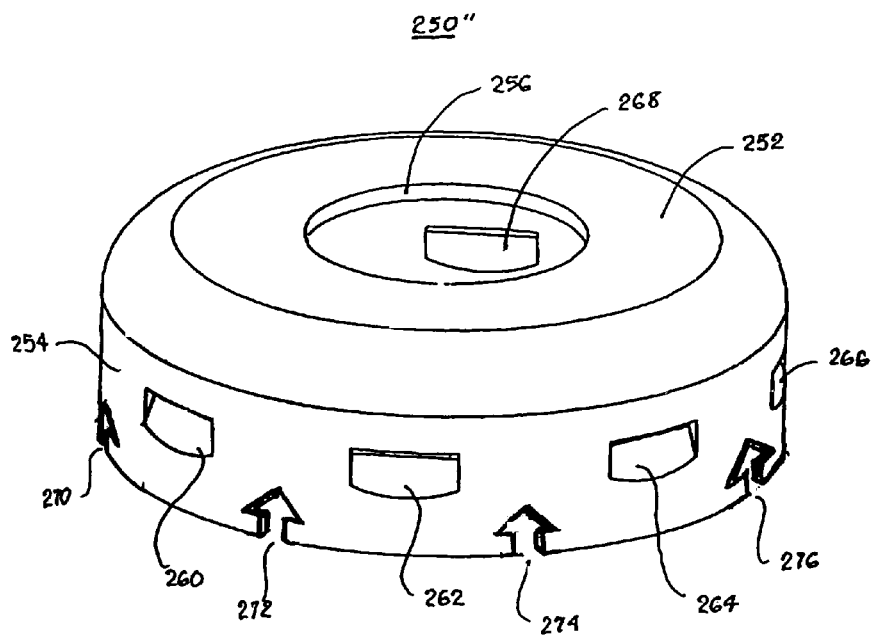
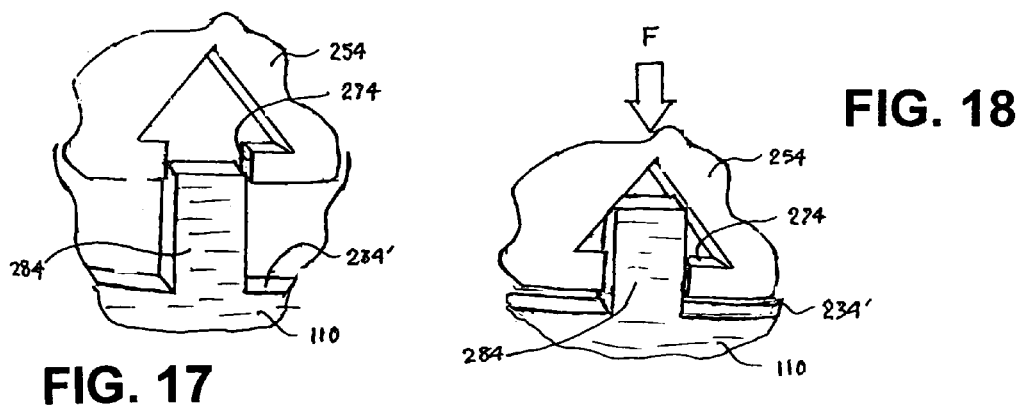
FIG. 18
FIG. 17
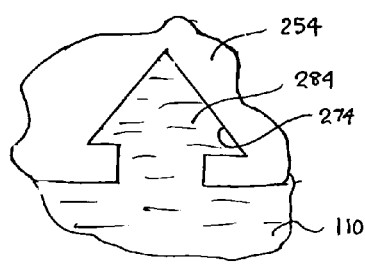
FIG. 19

CONNECTOR HEADER GROMMET FOR AN IMPLANTABLE MEDICAL DEVICE

REFERENCE TO RELATED APPLICATIONS

Reference is hereby made to U.S. patent application Ser. No. 10/199,601 filed Jul. 19, 2002, which is a continuation in part of U.S. patent application Ser. No. 09/767,796 filed Jan. 23, 2000, which is a continuation of U.S. patent application Ser. No. 09/417,157 filed Oct. 12, 1999 now abandoned, which is a continuation of U.S. patent application Ser. No. 09/159,119 filed Sep. 28, 1998, which is a divisional of U.S. patent application Ser. No. 08/904,636 filed Aug. 1, 1997, now abandoned all of which are herein incorporated by reference.

Reference is also made to commonly assigned U.S. patent application Ser. No. (P-11597) filed on even date herewith for CONNECTOR HEADER SETSCREW FOR AN IMPLANTABLE MEDICAL DEVICE in the names of Jennifer J. Zhao et al., and commonly assigned U.S. patent application Ser. No. (P-7670.07) filed on even date herewith for CONNECTOR HEADER FOR AN IMPLANTABLE MEDICAL DEVICE in the names of Kevin K. Tidemand et al.

FIELD OF THE INVENTION

The present invention pertains to connector headers of implantable medical devices (IMDs) for making electrical and mechanical connections with at least one connector element of an electrical medical lead.

BACKGROUND OF THE INVENTION

At present, a wide variety of IMDs are commercially released or proposed for clinical implantation in the human body. Certain IMDs are manufactured as discrete units that are intended to be selected by an implanting physician for a particular clinical use to be coupled together at implantation and to function as a unit. Typically, such IMDs comprise an implantable pulse generator (IPG) or a physiologic monitor and at least one elongated electrical medical lead that are electrically and mechanically connected together upon implantation. Such IMDs include for example implantable cardiac pacemakers for pacing one or more heart chamber, implantable cardioverter/defibrillators (ICDs) providing automatic cardioversion/defibrillation, anti-tachycardia pacing and bradycardia pacing functions of one or more heart chamber, cardiomyostimulators, cochlear implants, muscle and nerve stimulators, e.g., sacral nerve stimulators, spinal nerve stimulators and deep brain stimulators, and cardiac and other physiologic monitors.

The IPGs of cardiac pacemakers, ICDs, and the various tissue, organ and nerve stimulators typically comprise signal processing and/or pulse generating circuitry powered by a battery and enclosed within a hermetically sealed enclosure or housing, sometimes referred to as a "can", and a connector header attached to the housing that enables attachment of at least one elongated electrical medical lead. Certain implantable hemodynamic monitors also comprise a hermetically sealed housing and connector header that enables attachment of at least one elongated electrical medical lead. Other implantable monitors comprise a hermetically sealed housing and a sensor header that only supports a sensor, e.g., an EGM sense electrode.

The hermetically sealed housings are typically formed of a conductive biocompatible metal, although proposals have been made to form hermetically sealed housings of a non-conductive, biocompatible polymeric or ceramic. The opposed major sides of the IPG or monitor housing can be shaped having substantially circular, oval or rectilinear outlines and can have relatively straight and curved side edge sections. The opposed major sides are typically planar and disposed substantially in parallel, although the major sides may be bowed, convex or concave or otherwise contoured to some degree to conform to a particular implantation site. The opposed major sides are typically supported and joined together at their side edges by a mutual housing sidewall extending between them and having a sidewall width substantially defining the thickness of the hermetically sealed housing. The mutual sidewall extends through a number of sidewall turns or corners depending on the circular, oval or rectilinear outline or combination of such outlines of the opposed major sides. Generally speaking, such IPG and monitor housings are referred to as "prismatic".

The connector header for making a connection with a proximal connector assembly of an elongated electrical medical lead is physically attached to a header mounting section of the common sidewall that is typically, although no necessarily, planar. The connector header typically comprises a header body that is fabricated of a relatively hard, dielectric, non-conductive polymer encasing and isolating electrically conductive components from the patient's body. The connector header has a header thickness generally corresponding to the housing thickness and a header mounting surface that conforms to and is mechanically affixed against a mating housing sidewall mounting surface. The connector header has a header height measured in a direction extending away from the housing sidewall mounting surface and a header width measured in a direction extending along the housing header mounting surface in the width dimension of the housing. Various examples of connector headers and hermetically sealed housings are found in the patents referenced herein.

It is generally desirable that the connection of an electrical medical lead with an IPG or monitor be made rapidly and in a fail-safe manner during the initial implantation. Moreover, it is desirable to be able to explant the IPG or monitor at a later time in order to disconnect the electrical medical lead and either replace the IPG or monitor or replace the electrical medical lead.

Typical IPG and monitor connector headers are formed having at least one electrically conductive, header connector element or connector block embedded in the insulating material. Each connector block is connected by means of an insulated feed-through mounted to the hermetically sealed housing to the circuitry within the housing. Typical connector blocks are formed having a threaded bore for receiving a setscrew and a connector block bore extending at substantially right angles to the threaded bore for receiving a lead connector element. The connector block bore is axially aligned with a header connector bore extending from the connector block through the header body to an exterior surface thereof. The threaded bore and setscrew are axially aligned with a further header aperture extending from the connector block through the header body to an exterior surface thereof.

At implantation, the proximal connector assembly of the electrical medical lead is inserted into the header connector bore to locate a lead connector element, e.g., a lead connector pin or ring, within a connector block bore. A tightening tool, e.g., a hex wrench, is inserted through the further header aperture to engage a setscrew socket and rotate the setscrew against the lead connector element, thereby clamping the connector element against an inner surface of the connector block and ensuring electrical contact between a lead conductor of the electrical medical lead and the circuitry of the IPG or monitor. The attachment is reliable over long-term chronic implantation if the setscrew is properly tightened.

Over long-term chronic implantation, it is desirable to ensure that body fluids do not pass through the further header aperture and header connector bore to the connection made between the setscrew and the lead connector element within the connector block bore so that the IPG does not fail. Sealing rings are typically formed around the proximal connector assembly of the electrical medical lead that seal against the header connector bore upon insertion of the lead connector assembly into the header connector bore. Sealing or closing the further header aperture from fluid intrusion is a somewhat more difficult problem to solve, and various methods have been developed and implemented over the years.

In one approach, disclosed in U.S. Pat. No. 4,105,037, for example, the further header aperture is filled with a quantity of liquid silicone medical adhesive after the setscrew is tightened against the lead connector element. It is then necessary to wait for the silicone rubber adhesive to solidify before the implantation can be completed. This approach requires considerable care to complete without leaving voids and bubbles in the applied adhesive that body fluids can pass through. The cured silicone rubber adhesive is also difficult to remove after chronic implantation to be able to replace the electrical medical lead or the IPG or monitor.

In a further approach, various removable plugs have been proposed to fill the further header aperture to seal the setscrew and connector block from body fluids after the setscrew is tightened against the lead connector element as disclosed in U.S. Pat. Nos. 3,822,707, 3,908,668, 4,072,154, and 4,180,078, for example. The plug employed in the '154 patent is formed of a resilient silicone rubber or other biocompatible elastomer or elastomeric compound having an annular ring that fits into an annular groove of the further header aperture to retain the plug within the further header aperture. As shown in U.S. Pat. Nos. 4,141,752, 4,262,673 and 4,316,471, the plug is rigid like the header, and a resilient, silicone rubber, sealing O-ring is trapped and compressed between the plug sidewall and the further header aperture as the plug is inserted and tightened.

Fitting very small rigid or flexible plugs into the further header aperture is difficult, and they can be dislodged and lost during the procedure. The setscrew used to connect the electrode to the stimulator is quite small and if a plug is used to seal the setscrew, the plug is also quite small. From time to time, one or the other is lost on or near the operating table. In addition, due to their small size, both are quite difficult to handle directly by hand, which is quite undesirable during surgery. It is also not possible to immediately confirm that a fluid tight seal has been achieved.

In the '752 patent, the electrically conductive, metal setscrew is embedded within and physically attached to the plug so that the setscrew and plug screw are simultaneously rotated into the aligned setscrew connector bore and further header aperture by a tool engaging the plug to rotate it. The exterior surface of the plug is formed with a metal cap having a Phillips type cruciform opening that is engaged by a driver to rotate the integral cap and setscrew to tighten or loosen it. Again, the combined plug and setscrew can be mishandled, and it is also not always possible to confirm that a fluid tight seal has been achieved.

In U.S. Pat. No. 4,461,194, it is proposed to provide a tool for inserting a setscrew and a plug into the aligned threaded bore and further header aperture, respectively. The tool includes an elongated handle having a first wrench at one handle end and a second wrench at the other handle end. A rigid cap and a sealing member made of a soft sealing implantable medical grade elastomeric material are positioned on the first wrench with the rigid cap nearest the handle. A setscrew is positioned on the end of the wrench adjacent the sealing member and is preferably held on the end of the first wrench with a medical grade adhesive. The rigid cap is frictionally held in a predetermined spaced relationship from the setscrew, preferably, by a cylindrical tube frictionally engaging the periphery of the cap and fixedly attached to the handle portion. The rigid cap and the second wrench are designed such that the second wrench is used to drive the cap and compress the sealing member, thus providing a leak-proof seal. Again, there is a chance that the setscrew and plug will not remain on the handle during the procedure.

In a further approach that is in common use at the present time, the setscrew is partly screwed into the setscrew connector bore during manufacture. A pre-formed sealing member or element, typically referred to as a septum or a grommet, fills the header aperture aligned with the setscrew aperture (referred to in this context as a "grommet aperture") as disclosed, for example, in the above-referenced '668 patent and in U.S. Pat. Nos. 4,010,762, 4,479,489, 4,932,409, 5,207,218, 5,522,861, and 5,989,077. The pre-formed grommet is typically formed of flexible silicone rubber molded into a disc-shape having an inner end wall disposed toward the connector block and an outer end wall exposed to body fluids and tissue during implantation and a sidewall joining the end walls. A slit is typically formed through the grommet extending between the inner and outer end walls so that a hex wrench can be passed from the outer end wall through the pre-formed slit to engage the setscrew socket and rotate the setscrew. The pre-formed slit is expected to reseal and prevent fluid migration therethrough after the setscrew is withdrawn due to the soft pliant nature of the silicone rubber. At a later time, the IPG or monitor can be surgically exposed, and the hex wrench can be inserted through the pre-formed slit in the penetrable grommet to engage and rotate the setscrew away from the lead connector element, thereby releasing the connector element so that the lead connector assembly can be detached and withdrawn from the header connector bore.

Connector headers employing such penetrable grommets were typically fabricated as described in the above-referenced '668 patent to form a non-conductive, header body adhered to the IPG housing and about the electrically conductive components. The feedthrough pin(s) extending from the IPG housing were connected with the connector block(s), and disposable plug(s) or sleeve(s) were fitted into the connector block bore(s) to extend away from the connector block(s), a penetrable grommet(s) was fitted to extend from the setscrew(s), and a mold was fitted about the sub-assembly. The mold was filled with a biocompatible liquid epoxy, and the mold and disposable plug(s) or sleeve(s) were removed when the epoxy hardened to form a non-conductive, header body about the electrically conductive components. In the above-referenced '489 patent, it appears that a header grommet aperture was formed in the connector header body perhaps by use of a disposable plug, and the pre-formed penetrable grommet was adhered within the header grommet aperture employing an adhesive. The use of adhesive to retain the flexible plug is also suggested in the above-referenced '154 patent.

The penetrable grommet disclosed in the above-referenced '668 patent was quite large in diameter and thickness and was retained in place by molding the epoxy header body about the grommet to fit around an outwardly projecting ridge. Good adhesion was achieved between the epoxy header body and the silicone rubber grommet because of the ability to form such a mechanical interlock and because the thermosetting epoxy adhered well with silicone rubber as it solidified. Moreover, epoxy connector bodies remain relatively rigid and dimensionally stable during chronic implantation, so that separation and loss of adhesion does not readily occur. The use of the penetrable grommet simplified manufacturing and solved many of the problems associated with use of separate caps or plugs that the physician had to use to fill the further header aperture as described above, but other problems were observed over time.

The in situ molding process for forming the connector header body does not lend itself to mass production, since it does not involve use of interchangeable parts, and because the steps have to be done carefully and slowly. Bubbles, voids, surface blemishes and other defects can occur requiring rework or scrapping of the product. These drawbacks became more apparent and difficult to resolve as connector headers were reduced in size and incorporated increasing numbers of connector blocks and feedthroughs.

Consequently, a pre-formed, electrically insulating, dielectric, header body was developed as described in commonly assigned U.S. Pat. Nos. 4,142,532, 4,154,248, 4,182,345, and 4,226,244, and in U.S. Pat. No. 4,445,511, having pre-formed cavities, bores, and apertures for accommodating the connector block(s), feedthrough pin(s), pre-formed penetrable grommet(s), fixation mechanisms for attachment to the IPG or monitor housing, and for providing the header connector bore(s). Various attachment techniques for attaching the connector header body to the hermetically sealed housing involving use of mechanical locking components and adhesive backfilling of voids are also disclosed in these patents.

The pre-formed connector body can be formed of polyurethanes, e.g., PELLETHANE® urethane and TECOTHANE® urethane sold by Upjohn, Inc., a polysulfone, e.g., UDEL® polysulfone sold by Union Carbide, Inc., polymethylpentene, e.g., TPX® polymethylpentene sold by Mitsui and Company, polyvinylidene fluoride, e.g., KYNAR® polyvinylidene fluoride sold by the Allied Chemical, and ethylenechlorotrifluoroethylene, e.g., HALAR® ethylenechlorotrifluoroethylene sold by the Allied Chemical Corporation. Currently, pre-formed connector bodies used by the assignee of the present invention are injection molded of TECOTHANE® urethane because of its recognized biocompatibility and availability for use in IMDs.

The use of the pre-formed header body and these assembly techniques simplified assembly, reduced rework, and reduced chronic failure rate. Over time, such IPGs and monitors employing pre-formed header body fabrication techniques have been advantageously increased in capabilities and longevity while being reduced in thickness, height, and width, which define the displaced volume, and in weight. The reduction in the volume of the connector header has been achieved in part by substantially reducing the dimensions of the pre-formed penetrable grommets fitted into correspondingly reduced size header grommet apertures. However, problems have been observed as the size of the pre-formed penetrable grommets and the corresponding header grommet apertures have been reduced.

The passage of the hex wrench through the pre-formed slit is intended to displace, rather than remove the silicone rubber along the slit. However, the possibility of coring the pre-formed penetrable grommet by the hex wrench inserted through the pre-formed slit increases as the diameter of the pre-formed penetrable grommet is decreased. Even the proper insertion of the hex wrench through the pre-formed slit can cause coring of the silicone rubber and deposition of the cored silicone rubber within the setscrew socket. The cored slit cannot properly seal, and the silicone rubber lodged within the setscrew socket can block insertion of the hex wrench into the socket. The penetrable grommet must be designed to yield so as to move the displaced silicone rubber out of the way as the hex wrench is advanced through the slit.

As disclosed in the above-referenced '489 and '928 patents, a yield space between the inner surface of the grommet and the setscrew is provided to accommodate the silicone rubber of the grommet that is displaced inward by the advancing hex wrench. In the '928 patent, a rigid, ring-shaped, stiffener element is also embedded within the pre-formed grommet surrounding the yield space to stiffen the grommet and lessen the possibility of damage to the grommet by insertion of the hex wrench. Whether or not such an approach has merit, fabrication of such a pre-formed grommet with a rigid, ring-shaped, stiffener element may be difficult.

Even the proper insertion of the hex wrench through the pre-formed slit can also cause loss of adhesion of the grommet to the grommet aperture wall surrounding it unless the penetrable grommet is designed to yield and distribute stresses away from the grommet aperture wall as the hex wrench is advanced through the slit.

The mutual area of contact between the sidewalls of each pre-formed penetrable grommet and the header grommet aperture is necessarily reduced in order to reduce the overall volume of the connector header. The silicone rubber of the pre-formed penetrable grommet does not inherently adhere well with the material, particularly, TECOTHANE® urethane, of the pre-formed connector header body. Forming one or more retention ridge in the header grommet aperture sidewall to engage the sidewall of the silicone rubber grommet as shown in the above-referenced '928 patent, for example, is difficult if not impossible due to the injection molding of the pre-formed connector body from TECOTHANE® urethane.

Consequently, the low adhesion and reduced mutual area of contact between the grommet and header grommet aperture sidewalls has necessitated the use of a medical grade adhesive applied to between the grommet and header grommet aperture sidewalls before the pre-formed grommet is inserted into the header grommet aperture. The application of minute amounts of adhesive complicates assembly, and non-destructive testing of the resulting adhesion strength is difficult to accomplish. The applied adhesive can also intrude into the interior yield space and/or the socket of the setscrew. For these reasons, it would be preferable to eliminate use of adhesive to maintain the pre-formed grommet within the header grommet aperture Other problems have been observed with the use of silicone rubber to form such penetrable grommets and urethanes to form connector header bodies.

The epoxy or urethane connector header body and the silicone rubber grommet are both translucent and substantially colorless or of a slight color such that there is little visible contrast therebetween, rendering it difficult to visually distinguish a penetrable grommet from the surrounding connector header body and to locate the pre-formed slit. Physicians at times inadvertently insert the hex wrench through the pre-formed slit offset from the central axis of the penetrable grommet or at an improper angle and then have to move the hex wrench about or withdraw and reinsert it to properly seat the hex wrench tool end into the setscrew socket to rotate it. This could cause damage to the penetrable grommet compromising the ability of the pre-formed slit to reseal.

Moreover, the silicone rubber material is "sticky" and tends to adhere to itself across the pre-formed slit with aging so that the pre-formed slit tends to heal. After prolonged storage or chronic implantation, it becomes more difficult to insert a hex wrench through the pre-formed slit without coring or dislodging the penetrable grommet from the header grommet aperture. Sometimes, the pre-formed slit will not open at all, and the silicone rubber or the penetrable grommet is "punched out" when the hex wrench is advanced against it and into the underlying setscrew socket. The setscrew socket becomes plugged by the silicone rubber, and the penetrable grommet no longer seals.

It has also been found that connector header bodies formed of TECOTHANE® urethane exhibit cold flow or creep at points or surfaces where pressure is applied chronically. It has been observed that adhesion is lost between the grommet and header grommet aperture sidewalls when the grommet exerts pressure over time against the header grommet aperture sidewall causing expansion of the header grommet aperture diameter.

In addition, the TECOTHANE® urethane connector header body becomes slightly less rigid and dimensionally stable during chronic implantation in body fluids thereby aggravating the cold flow problem and negatively affecting adhesion with the silicone rubber grommet over time that can lead to spontaneous dislodgement of the grommet. Moreover, the weakened adhesion can be overcome if a replacement procedure requiring insertion of the hex wrench through the grommet slit occurs, and the grommet can be dislodged upon withdrawal of the hex wrench. It would be desirable to eliminate or accommodate the cold flow dimensional instability of the connector header body.

Further problems arise as the setscrews and connector blocks are miniaturized. Setscrews are typically formed without a head or "headless" having a uniform outer diameter extending between the socket end and the working or contact end. The setscrew working end is typically closed or solid, and the setscrew socket is a fraction of the length of the setscrew, limiting the depth of the setscrew socket that can be engaged by the hex wrench. As noted above, it can be difficult to locate such a shallow setscrew socket with the hex wrench, and adhesive and/or dislodged silicone rubber can block the shallow setscrew socket.

Size and fit tolerances of the setscrew thread and the threaded bore must be dictated to ensure that the setscrew can be easily rotated and tightened using a specified low torque applied to the setscrew tool or hex wrench. One problem that has occurred due to the tolerances and the involves the inappropriate positioning during manufacture or spontaneous movement of the setscrew within the threaded bore due simply to handling and shipment that cannot be observed when the setscrew is covered by the penetrable grommet. It has been observed that the setscrew can inadvertently migrate and intrude into the connector block bore to block insertion of a lead connector element into the connector block bore. The physician inserting the connector lead element into the connector block bore may incorrectly assume that it is properly inserted and tighten down the setscrew without making contact, resulting in a connection failure that may or may not be detected at the time of implantation.

In addition, the headless setscrew must be longer than the diameter of the connector block bore to prevent it from being unintentionally advanced all the way through the threaded bore and released into the connector bore. Moreover, tubular lead connector elements in current common use have a range of diameters, and the axially aligned connector header bores and connector block bores are provided in a corresponding range of diameters. Consequently, it has been necessary to either use a headless setscrew longer than the largest connector block bore diameter fitted into correspondingly long threaded bore or to provide a range of setscrews having lengths exceeding the connector block bore diameters. It would be desirable to simplify specification and costs of setscrews by employing a common setscrew for all such connector blocks.

Therefore, despite the improvements that have been made in connector headers over the years, problems remain to be solved in the design and fabrication of connector headers of the type employing penetrable grommets disposed in header grommet apertures overlying fasteners, e.g., setscrews, employed to attach lead connector elements with connector blocks of the connector header.

SUMMARY OF THE INVENTION

The preferred embodiments of the present invention incorporate a number of inventive features that address the above-described problems with penetrable grommets that may be combined with other features of the preferred embodiments or advantageously separately employed in connector headers of IMDs.

The connector headers for an IPG or monitor illustrated in the preferred embodiments incorporate a penetrable grommet entrapped within a header grommet aperture of a pre-formed header body to provide a fluid seal of a fastener, e.g., a setscrew within a threaded bore, of a connector block without the use of adhesive between the penetrable grommet and the header grommet aperture. An inner end wall of the disc-shaped penetrable grommet is disposed to face the setscrew, an outer end wall of the disc-shaped penetrable grommet is disposed to face outward in contact with body fluids, and a grommet sidewall bears against the sidewall of the header grommet aperture. Preferably, a pre-formed, resealable, slit extends axially between the outer and inner end walls of the disc-shaped, penetrable grommet.

In accordance with one aspect of the present invention, a ring-shaped retainer having a central bore that a tool, e.g., a hex wrench, can be passed through is disposed against an annular portion of the outer end wall and is affixed to an annular portion of the header body surrounding the annular portion of the outer end wall. Advantageously, substantially the full length of the pre-formed slit is disposed within the header grommet aperture below the ring-shaped retainer so that the contact between the grommet sidewall and the grommet aperture sidewall tends to provide a uniform pressure to the pre-formed slit between the outer and inner end walls of the disc-shaped, penetrable grommet.

The central bore of the ring-shaped retainer is aligned with the pre-formed slit and provides a visible target for precisely aligning and inserting the setscrew tool through the slit into operative engagement with the setscrew. Furthermore, the ring-shaped retainer can be substantially colorless or can be formed of a colored material contrasting from the substantially colorless or slightly colored connector header body and providing a visual target for precisely aligning and inserting the tool through the central bore and the slit into operative engagement with the setscrew.

In accordance with an aspect of the present invention, the cylindrical sidewall of the disc-shaped, penetrable grommet is formed having an irregular surface comprising a plurality of peaks and valleys that maintains fluid sealing contact with the cylindrical sidewall of the tubular header grommet aperture without adhesive therebetween. The nominal peak-to-peak outer diameter of the grommet can be specified to exceed the nominal inner diameter of the grommet aperture sidewall such that a low pressure interference fit is achieved upon insertion of the disc-shaped penetrable grommet into the header grommet aperture that reduces pressure applied against and resulting cold flow of the grommet aperture sidewall. Advantageously, the dimensional tolerances of the peak-to-peak diameter of the disc-shaped penetrable grommet and the inner diameter of the cylindrical sidewall of the tubular header grommet aperture can be relaxed to lower costs and to account for any changes in the nominal inner and outer diameters over chronic implantation. A low, uniform, interference pressure is attained over a wide tolerance upon assembly that is maintained even if the inner diameter of the cylindrical sidewall of the tubular header grommet aperture changes over extended time periods.

Preferably, the irregular surface comprises a plurality of sealing rings extending around the periphery of the grommet sidewall ensuring fluid sealing during chronic implantation. In addition, the sealing rings absorb stresses imposed when the setscrew tool is inserted through the pre-formed slit into engagement with the setscrew socket and moves the silicone rubber of the penetrable grommet outward against the grommet aperture sidewall.

Preferably, a yield space is formed in the inner end wall of the disc-shaped penetrable grommet to accommodate silicone rubber displaced inward by the advancement of the tool through the slit into the setscrew socket without stressing the attachment of the ring-shaped retainer to the connector header body.

In accordance with a still further aspect of the invention, the disc-shaped penetrable grommet is preferably formed of silicone rubber and an additive that diminishes the tackiness or stickiness of the mutually contacting silicone rubber surfaces that are formed by the slit made between the outer and inner end walls of the disc-shaped penetrable grommet. In this way, the formulated silicone rubber and additive diminishes the tendency to heal the slit over chronic implantation time.

In accordance with yet another aspect of the invention, the disc-shaped penetrable grommet is preferably formed of substantially colorless silicone rubber and an additive that pigments the penetrable grommet to provide visual contrast to the surrounding connector body material.

Preferably, the additive comprises titanium dioxide in a concentration of up to about 2% by weight. The titanium dioxide additive advantageously also colors the disc-shaped penetrable grommet opaque and thereby renders it more visible with respect to the transparent or translucent connector header body so that accurate insertion of the tool through the grommet slit is aided.

In accordance with a still further aspect of the invention, the setscrew is inhibited from being advanced during assembly or spontaneously into the connector block lumen intended to receive the lead connector element. The setscrew socket end engaged by the tool is preferably enlarged in diameter with respect to the threaded bore to limit advancement of the setscrew therein. The setscrew socket end is also preferably funnel shaped to eliminate a sharp cutting edge, to guide a setscrew tool end into the socket, and to provide a space accommodating any displaced silicone rubber of the penetrable grommet. The setscrew socket advantageously extends for substantially the full length of the setscrew to maximize setscrew socket depth and mutual contact area of the setscrew and the setscrew tool. In one embodiment of this aspect of the invention, the setscrew is shaped to have an enlarged diameter setscrew socket end. In another embodiment of this aspect of the invention, the setscrew socket end of an otherwise "headless" setscrew is preferably enlarged in diameter by a ring molded around the setscrew at the setscrew socket end to provide the enlarged diameter setscrew socket end.

In one preferred embodiment of this aspect of the invention, a setscrew retention space is provided between the inner end wall of the penetrable grommet and the connector block enabling the retraction of the setscrew to a retracted position with the setscrew substantially disposed within the setscrew retention space. After assembly, a setscrew tool is inserted through the penetrable grommet into the setscrew socket to rotate the setscrew. The setscrew is rotated until the enlarged diameter setscrew socket end is retracted into frictional engagement with the inner end wall of the penetrable grommet and the setscrew thread is substantially retracted out of the threaded bore, and the setscrew tool is withdrawn. The frictional engagement and retraction of the setscrew thread stabilizes the setscrew in the retracted position and inhibits spontaneous migration of the setscrew through the threaded bore into the connector block bore.

During implantation, a setscrew tool is inserted through the grommet slit into the setscrew socket and rotated to advance the setscrew threads along the threads of the threaded bore in the tightening direction until the setscrew working end engages the lead connector element. The application of the enlarged diameter setscrew socket end against the inner end wall of the penetrable grommet stabilizes the penetrable grommet from being unduly pressed inward by setscrew tool and minimizes punch out and coring of the penetrable socket.

The setscrew length can be optimized to minimize the threaded bore length and the length of the setscrew retention space regardless of the diameter of the connector block bore. The pitch and number of turns of the mating setscrew and threaded bore threads can be selected to provide movement of the setscrew between the retracted and advanced positions with a minimal number of turns of the setscrew tool. The setscrew and the threaded bore can be standardized for connector blocks having connector bores dimensioned to receive a wide range of lead connector element dimensions.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

FIG. 8 is an expanded perspective view of the retainer cap of FIGS. 5–7 illustrating the laterally extending retention elements in the cap sidewall for gripping the connector block body when the cap sidewall is inserted into the groove surrounding the grommet aperture as shown in FIGS. 6 and 7;

FIG. 9 is an exploded perspective view of a first embodiment of a setscrew and connector block of the present invention;

FIG. 16 is an expanded perspective view of a further embodiment of the retainer cap of FIGS. 5–7 illustrating notches formed in the cap sidewall for engagement with ridges formed in the groove when the cap sidewall is inserted into the groove surrounding the grommet aperture as shown in FIGS. 6 and 7;

FIG. 17 is a detail view of a tab formed in the groove about to be received in a notch formed in the cap sidewall of the retainer cap illustrated in FIG. 16 when the cap sidewall is inserted into the groove;

FIG. 18 is a detail view of the tab formed in the groove received in the notch of FIG. 17 and the application of ultrasonic energy to the retainer cap to heat and melt the thermoplastic material of the tab contacting the cap sidewall; and FIG. 19 is a detail view of the thermoplastic material of the tab melted into and filling the notch of FIGS. 17 and 18 following application of ultrasonic energy to the retainer cap.

DETAILED DESCRIPTION OF THE PREFERRED EMBODIMENTS

In the following detailed description, references are made to illustrative embodiments of methods and apparatus for carrying out the invention. It is understood that other embodiments can be utilized without departing from the scope of the invention. Methods and apparatus are described for attaching lead connector elements of electrical medical leads received within connector bores of connector headers attached to hermetically sealed enclosures of IPGs or monitors of any of the types known in the art.

Figure 1:
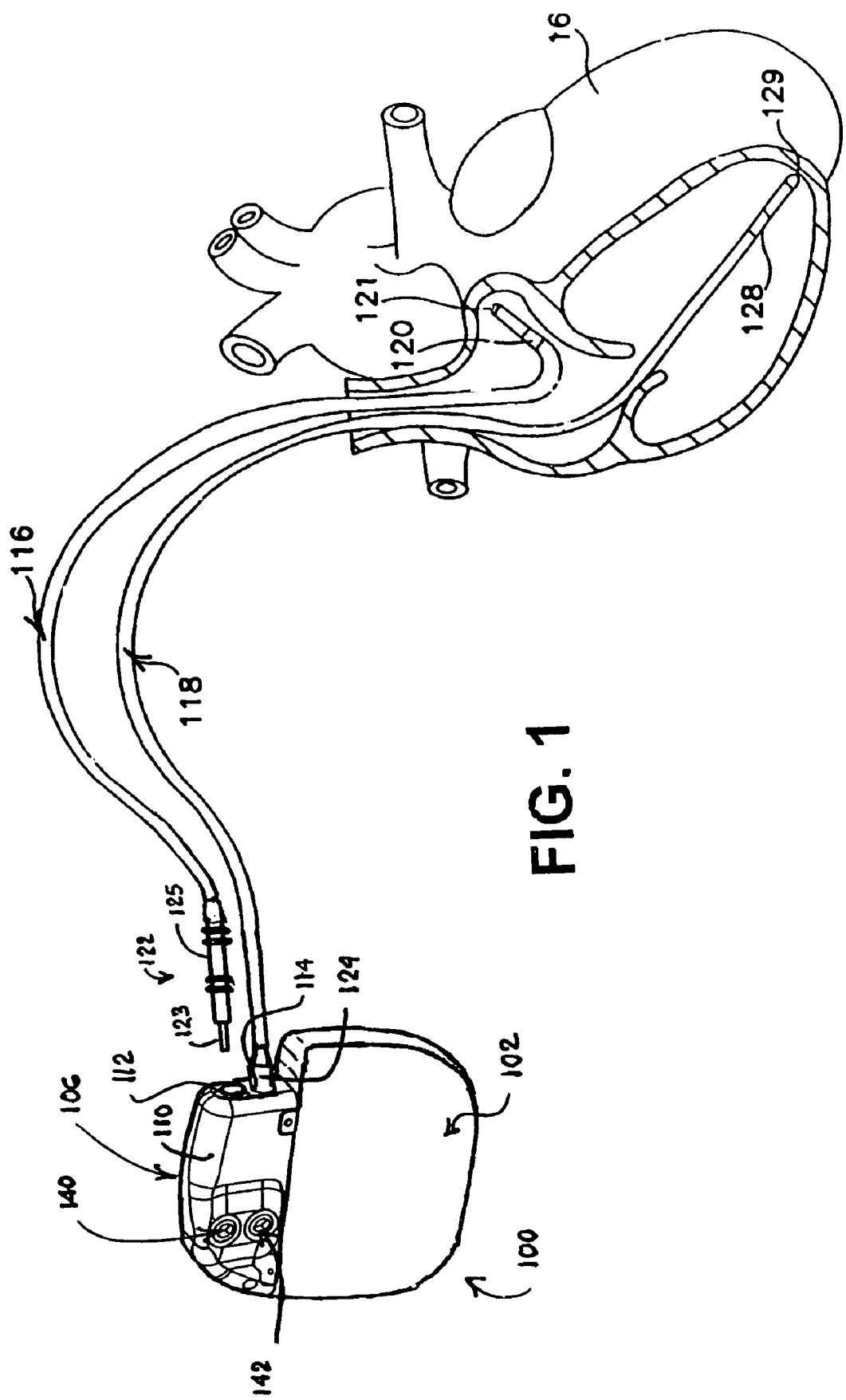
FIG. 1 is a perspective view of an exemplary IMD comprising a pacemaker IPG and atrial and ventricular electrical medical leads in which the inventive features of connector headers may be incorporated in combination or separately.

For example, a pacemaker IPG 100 is illustrated in FIG. 1 adapted to be attached to a bipolar atrial endocardial pacing lead 116 and attached to a bipolar ventricular endocardial pacing leads 118 extending in a transvenous pathway from the subcutaneous site of implantation of the IPG 100 into the right atrium and right ventricle of a patient's heart 16, respectively. The bipolar atrial endocardial pacing lead 116 comprises an elongated lead body enclosing a pair of electrically insulated lead conductors each extending from a connector element of proximal lead connector assembly 122, e.g., a connector pin 123 and a connector ring 125, and one of distal tip and ring pace/sense electrodes 121 and 120, respectively. Similarly, the bipolar ventricular endocardial pacing lead 118 comprises an elongated lead body extending between proximal lead connector assembly 122, e.g., a connector pin or a connector ring (obscured in the view), and one of distal tip and ring pace/sense electrodes 129 and 128, respectively. The bipolar endocardial pacing leads 116 and 118 can take any of the forms known in the art of pacing and cardioversion/defibrillation lodged in heart chambers or cardiac vessels or disposed on the epicardial surface of the heart 16 as is known in the art. Typically, in bipolar cardiac pacing leads, one electrical conductor extends between a proximal connector pin, e.g., connector pin 123, and a distal tip electrode, e.g., pace/sense electrode 121, and a second electrical conductor extends between a connector ring distal to the proximal connector pin, e.g., connector ring 125, and the ring electrode, e.g., pace/sense electrode 120.

The pacemaker IPG 100 comprises a hermetically sealed housing 102 that encases a battery and circuitry and electrical components powered by the battery to process atrial and ventricular cardiac signals and generate atrial and/or ventricular pacing pulses to synchronously pace the atria and ventricles as needed in a manner well known in the art. The pacemaker IPG 100 also comprises a connector header 106 formed of for example, a dielectric header body 110 injection molded of TECOTHANE® urethane as described above. The header body 110 is formed having an elongated header connector bore 112 for receiving the bipolar atrial lead connector assembly 122 and a ventricular lead header connector bore 114 for receiving the bipolar ventricular lead connector assembly 124.

Figure 2:
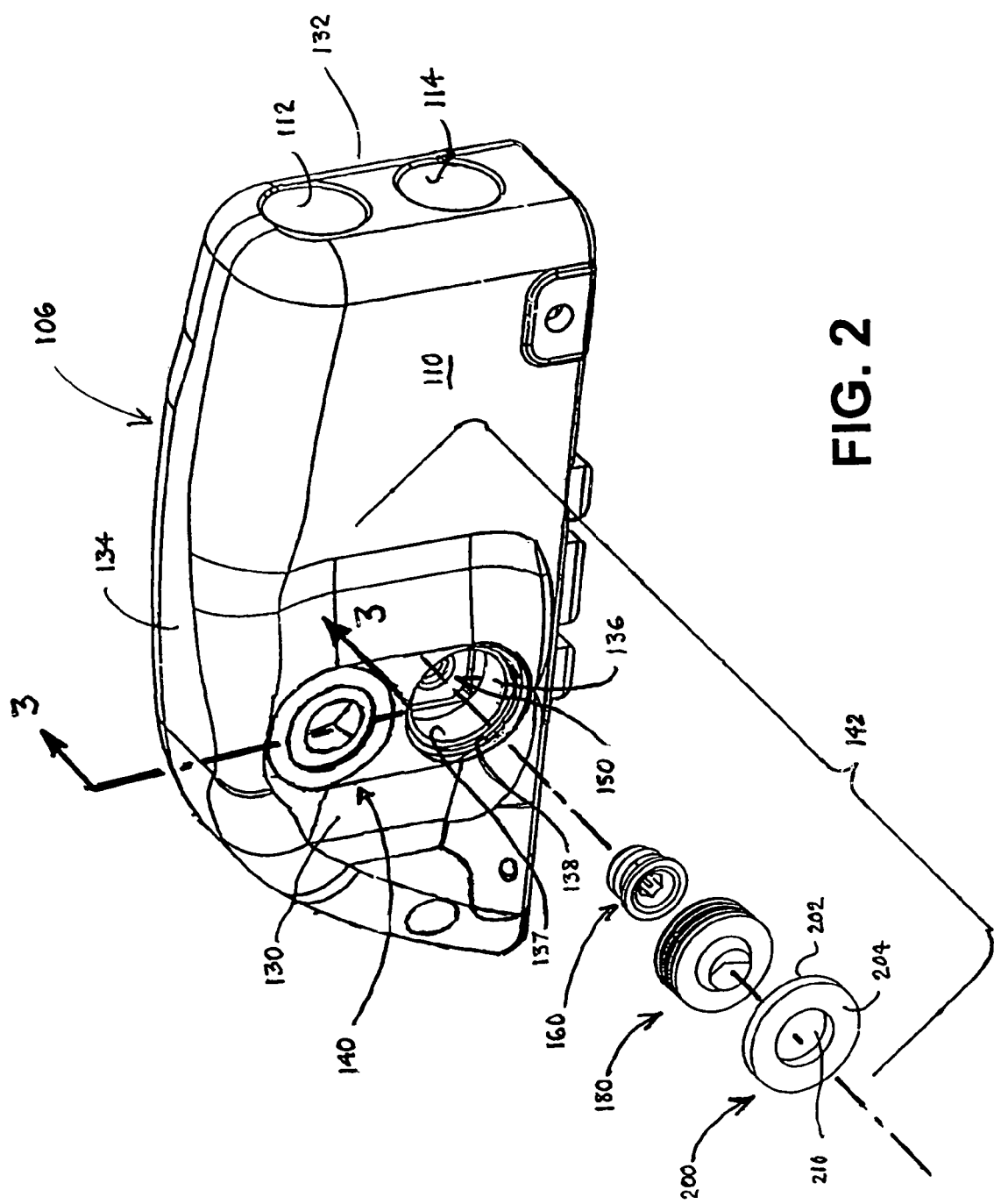
FIG. 2 is a perspective view of a first embodiment of the pacemaker IPG connector header of FIG. 1 with a setscrew, penetrable grommet, and ring-shaped retainer illustrated in relation to a grommet aperture and connector block within a cavity of the connector header body.

In FIGS. 1 and 2, two pin connector assembles 140 and 142 incorporating aspects of the present invention that can be accessed from one side 130 of the pre-formed header body 110 are depicted. It will be understood that two similar ring connector assemblies that are obscured from view by the pre-formed header body 110 can be accessed from the opposite side 132 of the pre-formed header body 110. It will be understood that all of the pin and ring connector assemblies could be oriented to be viewed and accessed from the same side 130 or 132. Alternatively, at least the pin and/or ring connector assembly for connecting the connector pin and/or ring of the bipolar atrial pacing lead 116 could be accessed from the top 134 of the pre-formed header body 110.

In the illustrated embodiments, the atrial header connector bore 112 and associated pin and ring connector assemblies are disposed above the ventricular header connector bore 114 and its associated pin and ring connector assemblies in this particular embodiment. Alternatively, the atrial and ventricular header connector bores 112 and 114 and associated pin and ring connector assemblies could be disposed in side-by-side relation. The number of header connector bores of the connector header 106 and the number of connector assemblies associated with each header connector bore can vary considerably depending upon the type of IPG or monitor and electrical medical leads selected to be coupled to the connector header 106.

It will be understood that the ring and pin connector block bore diameters, the spacing of the pin and ring connector blocks, and the diameters along the lengths of the header connector bores 112 and 114 are selected to conform to a proprietary standard or an industry recognized standard, e.g., the IS-1 standard. For example, Medtronic, Inc. presently manufactures ICD IPGs with four basic connector designs, designated configurations "B", "C", "D", and "E". The "B" configuration includes three 6.5 mm connector bores for receiving high voltage electrical lead connectors of the type used to couple to cardioversion/defibrillation electrodes and one IS-1 compatible 3.2 mm in-line electrical connector bore for receiving an IS-1 electrical lead connector of the type generally used to couple to cardiac pacing and sensing electrodes. The "C" configuration includes a single 3.2 mm "DF-1" connector bore for receiving high voltage electrical lead connectors used to couple to cardioversion/defibrillation electrodes and a single IS-1 connector bore. The "D" configuration includes three DF-1 connector bores and one IS-1 connector bore. The "E" configuration includes two 6.5 mm connector bores and two 5 mm connector bores for receiving electrical lead connectors used to couple to individual cardiac pacing and sensing electrodes.

Figure 3:
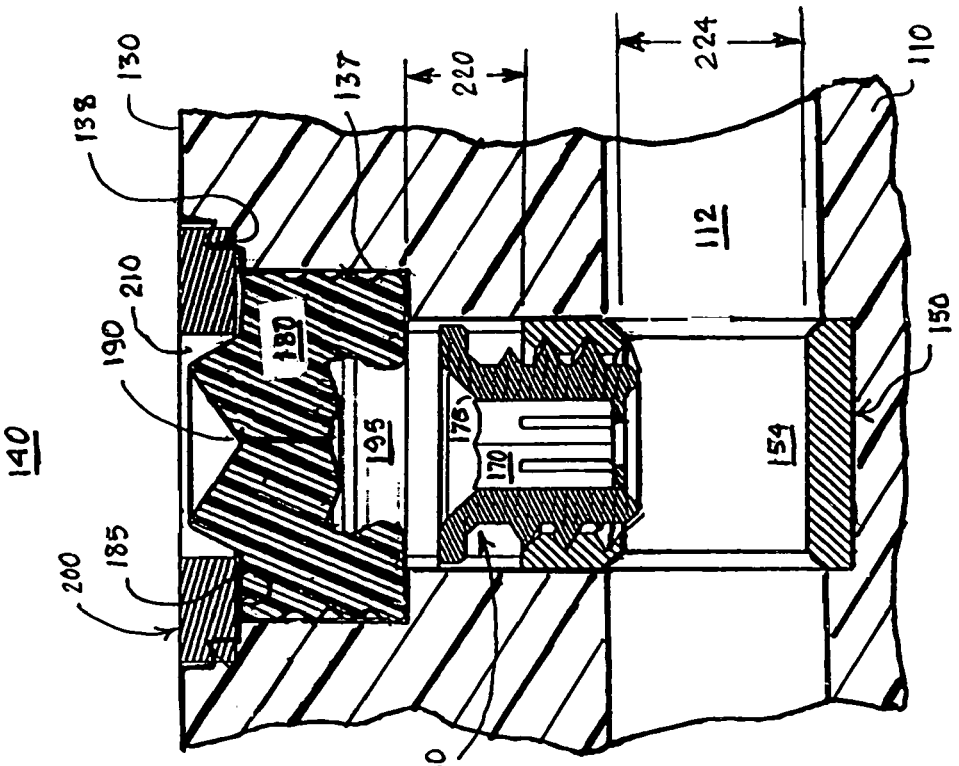
FIG. 3 is a cross-section view taken along lines 3—3 of FIG. 2 illustrating the ring-shaped retainer, the penetrable grommet within the grommet aperture, and the connector block within the connector header body with the setscrew in a partially advanced position to bear against a lead connector element within the connector bore.
Figure 4:
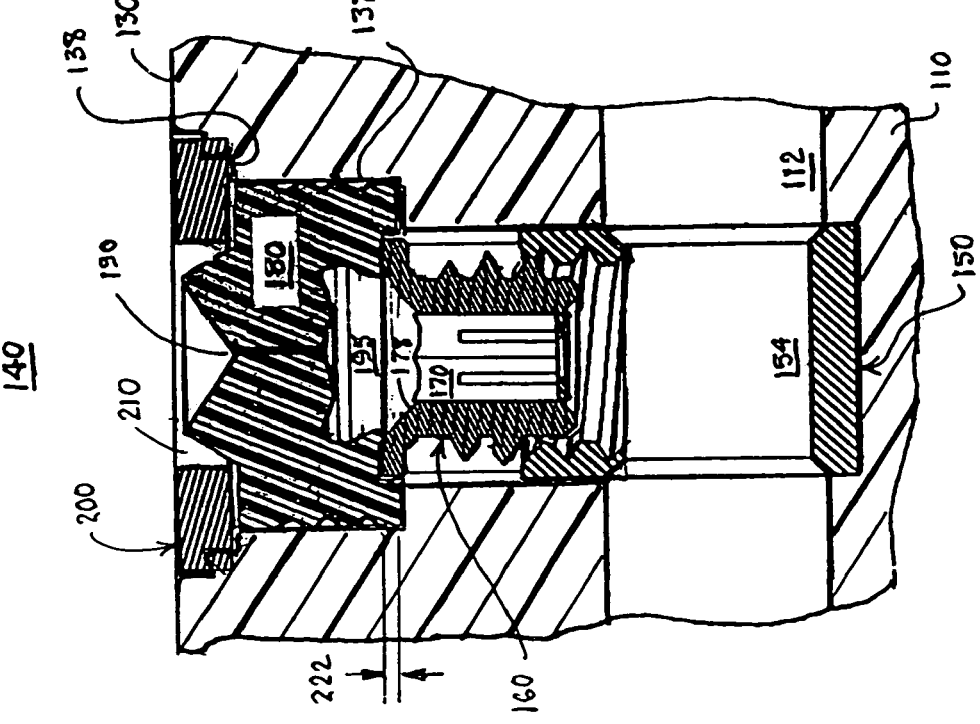
FIG. 4 is a cross-section view taken along lines 3—3 of FIG. 2 illustrating the ring-shaped retainer, the penetrable grommet within the grommet aperture, and the connector block within the connector header body with the setscrew in the retracted position to frictionally engage against the grommet inner end wall to inhibit unintentional rotation and movement to the advanced position of FIG. 3.
Figure 5:
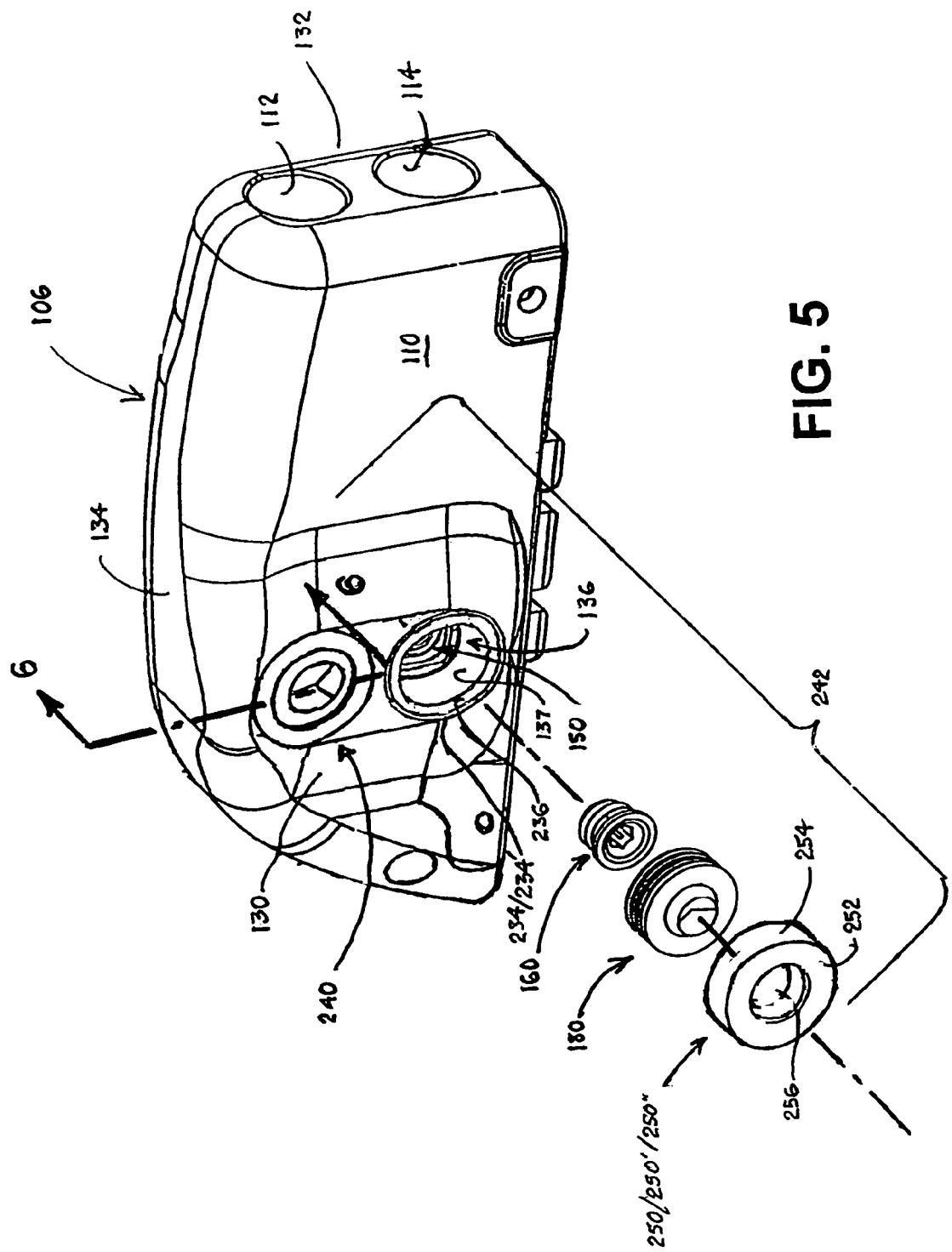
FIG. 5 is a perspective view of a second embodiment of the pacemaker IPG connector header of FIG. 1 with a setscrew, penetrable grommet, and a retainer cap illustrated in relation to a grommet aperture and connector block within the connector header body.

Regardless of the number and orientation of the four connector assemblies 140, 142 etc., each comprises a connector block 150, a setscrew 160, a penetrable grommet 180 and a ring-shaped retainer 200 arranged as shown in FIGS. 2–4. The advanced and retracted positions of the setscrew 160 with respect to the connector block 150 and the penetrable grommet 180 are depicted in FIGS. 3 and 4. In this embodiment, a tubular grommet aperture 136 having a cylindrical grommet aperture sidewall 137 extends from side 130 into the header body 106 transverse to the axis of header connector bore 114. An annular seat 138 is formed around the grommet aperture 136. The ring-shaped retainer 200 is preferably formed of a dielectric thermoplastic material and is sized in outer diameter to be fitted into the annular seat 138 and thermally welded to the material of the connector header body 110. The annular seat 138 preferably includes an annular ridge of other enhancement that facilitates thermal bonding of the ring-shaped retainer 200 to the annular seat as described further below.

In the exploded view of the components of the connector assembly 142 depicted in FIG. 2, one such connector block 150 fitted into a cavity within the pre-formed header body 110 is exposed for view though the grommet aperture 136. Each connector block 150 is electrically connected to the circuitry within the housing 102 by a connector pin of a feedthrough (not shown) that is mounted to extend through the wall of hermetically sealed housing 102 in a manner well known in the art. In the particular illustrated embodiments, atrial and ventricular pin and ring connector blocks 150 are disposed and spaced apart in cavities along the respective atrial and ventricular header connector bores 112 and 114 by a spacing corresponding to the spacing between the connector pins and rings (not shown) of the atrial and ventricular lead connector assemblies 122 and 124.

In reference to FIG. 9, each connector block 150 is formed of stainless steel, for example, and has a threaded bore 152 intersecting a connector block bore 154 such that the connector block bore 154 extends transversely to the threaded bore 152. A spiral thread 156 is formed in the threaded bore 152. The connector block bore 154 has a bore diameter 156 sized to receive a lead connector pin or ring, and each connector block bore 152 is axially aligned with the axis of one of the header connector bores 112 or 114. Typically, the bore diameter 156 of a connector block 150 employed to attach a lead connector pin is smaller than the bore diameter 156 of a connector block 150 employed to attach a lead connector ring.

Figure 10:
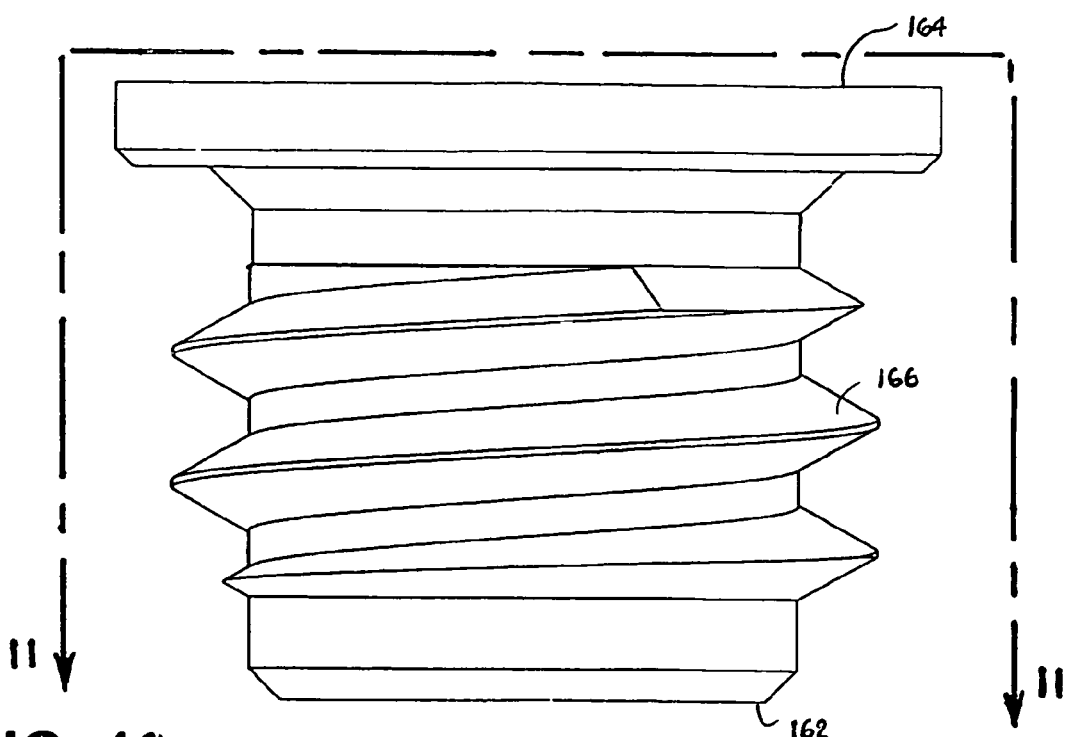
FIG. 10 is a side view of the setscrew illustrated in FIG. 9.
Figure 11:
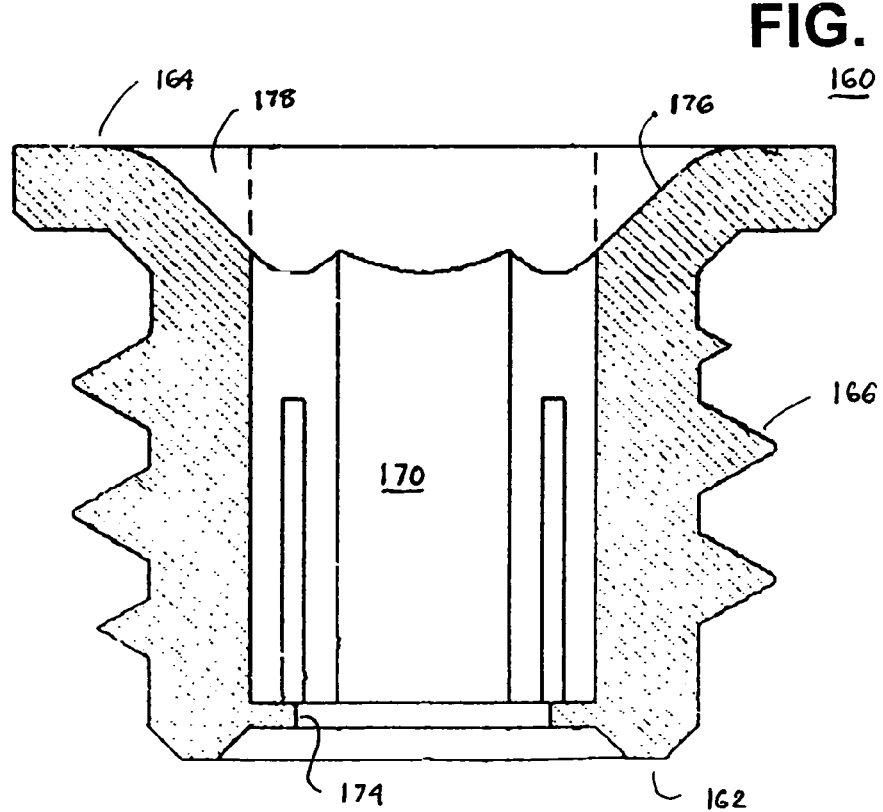
FIG. 11 is a side cross-section view taken along lines 11—11 of FIG. 10 of the setscrew illustrated in FIGS. 9 and 10.

In reference to FIGS. 9–11, a first embodiment of a setscrew 160 adapted to be threaded into the threaded bore 152 is depicted. The setscrew extends between a setscrew working end 162 and a setscrew socket head 164, and a spiral thread 166 is formed around the circumference thereof. The spiral thread 166 corresponds dimensionally and in pitch to the spiral thread 158 or the threaded bore 152 so that the setscrew 160 can be moved between a retracted position depicted in FIG. 3 and an advanced position depicted in FIG. 4. The setscrew socket 170 can take any shape that can receive a setscrew tool, e.g., a hexagonal shape that is sized to receive a hex wrench setscrew tool.

The setscrew socket head 164 is enlarged in diameter surrounding the opening to the setscrew socket 170 with respect tot eh diameter of the threaded bore 152. The setscrew 160 is inhibited by the enlarged diameter setscrew socket head 164 from being advanced during assembly or spontaneously beyond the advanced position depicted in FIG. 4 and all the way through the threaded bore 152 and into the connector block lumen 154 intended to receive the lead connector element. The enlarged diameter setscrew socket head 164 is formed with a funnel-shaped opening 176 that guides a hex wrench passed through the penetrable grommet 180 into the setscrew socket 170. The funnel shape also eliminate a sharp cutting edge at the opening of the setscrew socket 170 that could shear any silicone rubber of the penetrable grommet 190 that is pushed into the socket opening by the advancing hex wrench. The funnel shape also provides an annular space 178 to receive any such silicone rubber of the penetrable grommet 190 that is pushed toward the socket opening or otherwise displaced by the advancing hex wrench.

Typical prior art setscrews are formed with a closed setscrew working end 162 resulting in a relatively short setscrew socket. The setscrew socket 170 advantageously extends for substantially the full length of the setscrew between the annular space 178 and the setscrew working end 162 to maximize the depth of the setscrew socket 170 and the mutual contact area of the setscrew socket walls and the setscrew tool inserted into the setscrew socket 170. In accordance with the present invention, a hex wrench stop ring 174 is formed at the setscrew working end that blocks advancement of the hex wrench all the way through the setscrew socket 170.

Figure 14:
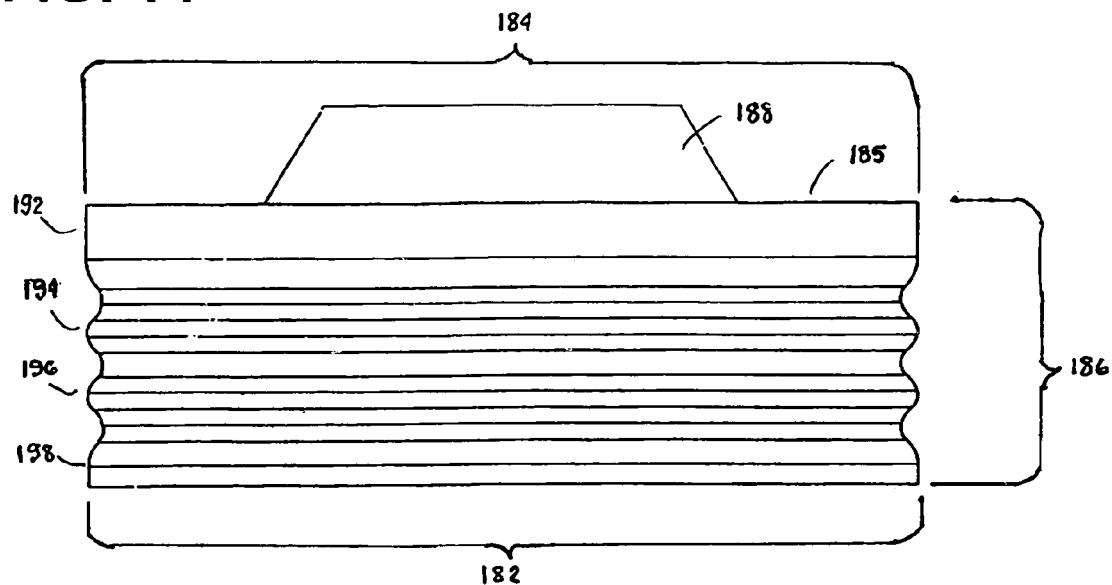
FIG. 14 is an expanded side view of the penetrable grommet of the present invention.
Figure 15:
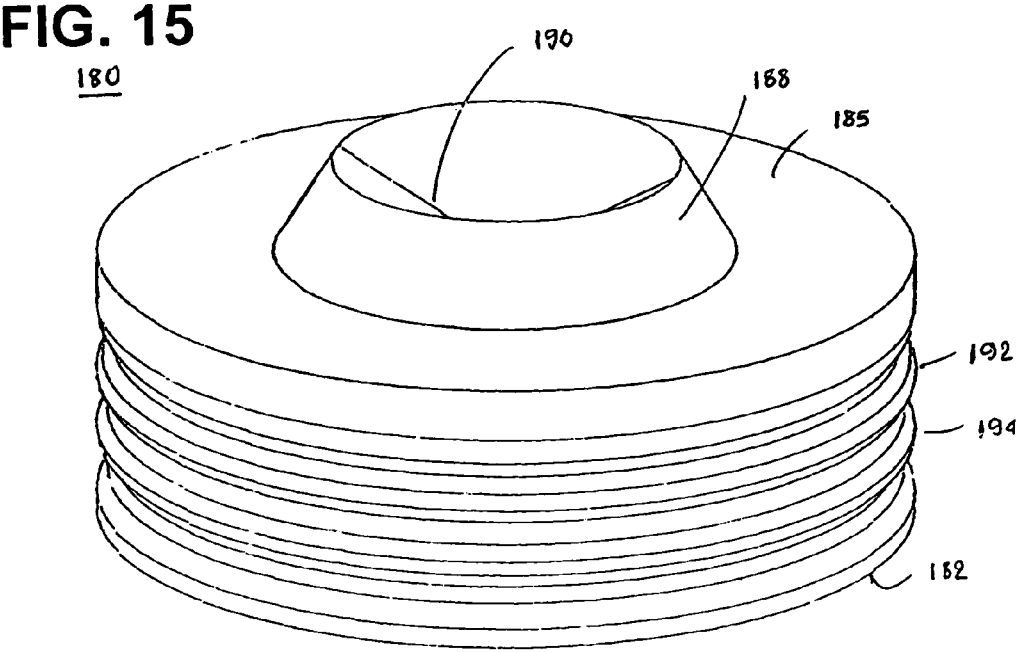
FIG. 15 is an expanded perspective view of the penetrable grommet of the present invention.

The penetrable grommet 180 (shown enlarged in FIGS. 14 and 15 and in side section view in FIGS. 3 and 4) is entrapped within the header grommet aperture 136 of the pre-formed header body 110 by the retainer 200 as described further below. The penetrable grommet 180 provides a fluid seal of the setscrew 160 within the threaded bore 152 of a connector block 150 without the use of adhesive between the penetrable grommet 180 and the header grommet aperture 136.

An inner end wall 182 of the disc-shaped penetrable grommet 180 is disposed to face the setscrew 160, and an outer end wall 184 of the disc-shaped penetrable grommet 180 is disposed to face outward in contact with body fluids. The outer end wall 184 preferably comprises a circular, outwardly projecting portion 188 surrounded by an annular, substantially flat or planar portion 185. A grommet sidewall 186 extends between the inner and outer end walls 182 and 184 that bears against the sidewall 137 of the header grommet aperture 136.

A self-sealing passage, e.g., a pre-formed slit 190, extends axially between the outer and inner end walls 182 and 184 of the disc-shaped penetrable grommet 180. The pre-formed slit 190 preferably extends laterally across the central axis of the disc-shaped penetrable grommet 180 within the circular, outwardly projecting portion 188. The pre-formed slit can take any of the known forms, including a single cut bisecting the central axis of the disc-shaped penetrable grommet 180 as depicted in the above-referenced '489 patent or a Y-shaped or a cross shaped slit centered on the central axis of the disc-shaped penetrable grommet 180.

The cylindrical sidewall 186 of the disc-shaped, penetrable grommet 180 is preferably formed having an irregular surface comprising a plurality of peaks and valleys that maintains fluid sealing contact with the cylindrical sidewall of the tubular header grommet aperture without adhesive therebetween. In one embodiment, the irregular surface comprises a corrugated surface attained by a plurality of sealing ring(s) 192, 194, 196, 198 extending around the periphery of the grommet sidewall 186 ensuring fluid sealing between the grommet sidewall 186 and the grommet aperture sidewall 137 during chronic implantation. The nominal peak-to-peak outer diameter of the penetrable grommet 180 can be specified to exceed the nominal inner diameter of the grommet aperture sidewall 137 such that a low pressure interference fit is achieved upon insertion of the disc-shaped penetrable grommet 180 into the header grommet aperture 136 that reduces pressure applied against and resulting cold flow of the grommet aperture sidewall 137. Advantageously, the dimensional tolerances of the peak-to-peak diameter of the disc-shaped penetrable grommet 180 and the inner diameter of the grommet aperture sidewall 137 can be relaxed to lower costs and to account for any changes in the nominal inner and outer diameters over chronic implantation. A low, uniform, interference pressure is attained over a wide tolerance upon assembly that is maintained even if the inner diameter of the header grommet aperture 136 changes over extended time periods. In addition, the sealing rings 192, 194, 196, 198 absorb stresses imposed when the setscrew hex wrench is inserted through the slit 190 into engagement with the setscrew socket and moves the silicone rubber of the penetrable grommet 180 outward against the grommet aperture sidewall 137. In effect, the corrugated surface of the grommet sidewall 186 flattens against the grommet aperture sidewall 137.

A central, circular yield space 195 in one embodiment corresponding substantially in diameter to the diameter of the circular, outwardly projecting portion 188 is formed in the inner end wall 182 of the disc-shaped penetrable grommet 180 as shown in FIGS. 3 and 4. The yield space 195 accommodates silicone rubber displaced inward by the advancement of the setscrew hex wrench through the slit 190 into the setscrew socket 170 without stressing the attachment of the ring-shaped retainer 200 to the connector header body 110.

Header body 110 is substantially colorless, which for reference is characterized herein as a first color. The substantially colorless, silicone rubber, penetrable grommet 180 can be difficult to visually distinguish from the header body 110, and the pre-formed slit 190 can heal over time. The disc-shaped, penetrable grommet 180 is therefore preferably formed of silicone rubber and an additive that diminishes the tackiness or stickiness of the mutually contacting silicone rubber surfaces that are formed by the slit 190 made between the outer and inner end walls 182 and 184. In this way, the formulated silicone rubber and additive diminishes the tendency to heal the slit 190 over chronic implantation time. The additive additionally or alternatively, colors the substantially colorless silicone rubber to provide visual contrast to the surrounding connector body material.

Preferably, the additive comprises titanium dioxide in a concentration of up to about 2% by weight. The titanium dioxide additive advantageously also colors the disc-shaped penetrable grommet 180 opaque and thereby renders it more visible with respect to the transparent or translucent connector header body 110 so that accurate insertion of the setscrew hex wrench through the grommet slit 190 is aided.

In the embodiment of the invention depicted in FIGS. 2–4, the ring-shaped retainer 200 is formed of a thermoplastic material in the shape of a washer having retainer inner and outer annular sides 202 and 204 and a central opening 210. An outer band of the inner annular side 202 is thermally welded to the annular portion or seat 138 of the header body 110 as shown in FIGS. 3 and 4 after the setscrew 160 is screwed into the threaded bore 152 and the penetrable grommet is fitted into the grommet aperture 136. The thermal welding can be accomplished employing ultrasonic welding techniques or heat staking techniques.

Ultrasonic welding techniques of the type described in the above-referenced Publication No. 2003/0040780 may be employed to effect the thermal welding. Ultrasonic energy delivered by a shaped ultrasonic head or horn to two thermoplastic pieces to be joined vibrates the pieces resulting in heat energy that melts a mass of the thermoplastic material in the area of mutual contact. In this regard, an outer band of the inner annular side 202 and the annular portion or seat 138 of the header body 110 are preferably configured to enhance mutual melting and thermal bonding without appreciably distorting the external appearance of the ring-shaped retainer 200. Such enhancement can include shaping the outer band of the inner annular side 202 and the annular portion or seat 138 to matingly engage through a tongue and groove joint, a step joint or a shear joint or the like. Or, a sharp edged annular ridge can be formed extending away from the outer band of the inner annular side 202 or the annular portion or seat 138 of the header body 110 so that an edge contact is made when the outer band of the inner annular side 202 is applied against the annular portion or seat 138. In this way, the ultrasonic energy applied to the outer annular side 204 by the shaped head or horn of an ultrasonic generator concentrates at the line or lines of contact and heat is generated to cause melting and adhesion upon cooling.

After thermal welding of the ring-shaped retainer to the annular portion or seat 138 of the header body 110, an inner band of the inner annular side 202 bears against the annular, substantially flat or planar portion 185 of the grommet outer end wall 184 to hold the penetrable grommet 180 in the grommet aperture 136. The circular, outwardly projecting portion 188 of the penetrable grommet 180 extends through the circular central opening 210 so that the slit 190 can be accessed.

The central bore 210 of the ring-shaped retainer 200 is aligned with the pre-formed slit 190 and provides a visible target and guide for precisely aligning and inserting the hex wrench through the central opening 210, the slit 190, the central, circular yield space 195, and into the setscrew socket 170. The ring-shaped retainer 200 can be substantially colorless or can be formed of a colored material contrasting from the substantially colorless connector header body 110 and providing a more visible target and guide. The funnel shaped opening 176 of the setscrew socket 170 also assists in guiding the hex wrench into the socket 170 without shearing silicone rubber from the penetrable grommet 180.

Referring to FIGS. 3 and 4, a setscrew retention cavity or space 220 is provided between the inner end wall 182 of the penetrable grommet 180 and the connector block 150 enabling the retraction of the setscrew 160 to a retracted position depicted in FIG. 3 with the setscrew 160 substantially disposed within the setscrew retention space 220. After assembly, a setscrew hex wrench is inserted through the penetrable grommet slit 190 into the setscrew socket 170 to rotate the setscrew 160 to back it out of the threaded bore 152. The setscrew 160 is backed out from the position depicted in FIG. 4 to the position depicted in FIG. 3 until the enlarged diameter setscrew socket end 164 is in frictional engagement with an annular portion of the inner end wall 182 of the penetrable grommet 180 surrounding the circular yield space 195. The silicone rubber of the penetrable grommet 180 is displaced outward a distance 222, and the setscrew spiral thread 166 is substantially retracted out of engagement with the spiral thread 158 or the threaded bore 152. The setscrew hex wrench is withdrawn, and the frictional engagement and retraction of the setscrew thread 166 stabilizes the setscrew 160 in the retracted position of FIG. 3 and inhibits spontaneous migration of the setscrew 160 through the threaded bore 152 and into the connector block bore 154. The finished IPG 100 is stored and shipped with all setscrews 160 in the retracted position of FIG. 3.

The setscrew length can be optimized to minimize the threaded bore length and the length of the setscrew retention space 220. The pitch and number of turns of the mating setscrew and threaded bore threads 166 and 158 can be selected to provide movement of the setscrew 160 between the retracted and advanced positions with a minimal number of turns of the setscrew hex wrench. The setscrew 160 and the threaded bore 152 can be standardized for connector blocks having connector bores dimensioned in diameter 224 to receive a wide range of lead connector element dimensions because advancement of the setscrew 160 completely through the threaded bore 152 is prevented when the enlarged diameter setscrew head contacts the connector block 150.

It should be noted that the full length of the resealable slit 190 is disposed within the grommet aperture 136 below the ring-shaped retainer 200 bearing against the annular portion 185 of the outer end wall 182 of the penetrable grommet 180. Thus, a substantially constant compression force is applied across the slit 190 from the inner end wall 182 to the outer end wall 184 due to the interference fit and slight compression of the rings 192, 194, 196, 198 of the grommet sidewall 186 against the cylindrical grommet aperture sidewall 136. Therefore, the tendency of prior art resealable slits to open and admit fluids due to an uneven application of compressive force, particularly diminished compressive force at the outer end wall, is minimized.

As noted above, the IPG 100 is shipped with all setscrews 160 in the retracted position of FIG. 3. During implantation, a setscrew hex wrench is inserted through the grommet slit 190 into the setscrew socket 170 and rotated to advance the setscrew spiral thread 166 along the spiral thread 158 of the threaded bore 154 in the tightening direction until the setscrew working end 162 engages a lead connector element inserted through the connector block bore 154. It is not possible to tighten the setscrew 160 any further once the enlarged diameter setscrew socket head 164 contacts the connector block 150. Therefore it is not possible to accidentally advance the setscrew fully into the connector block bore 154.

When a hex wrench is inserted through the resealable slit 190, it displaces the silicone rubber of the penetrable grommet 180 laterally to effectively flatten the grommet sidewall 186 and inward into the circular yield space and the annular space 178. Shearing of silicone rubber and plugging of the setscrew socket 170 is avoided.

Figure 12:
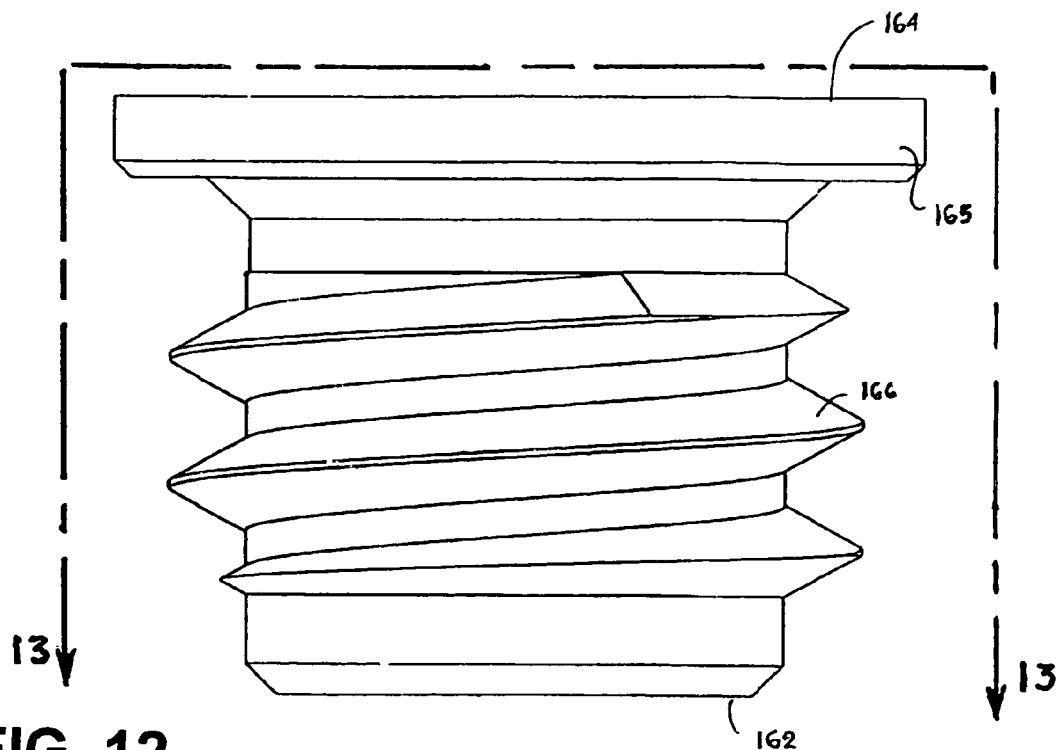
FIG. 12 is a side view of second embodiment of a setscrew adapted to be used with the connector block illustrated in FIG. 9.
Figure 13:
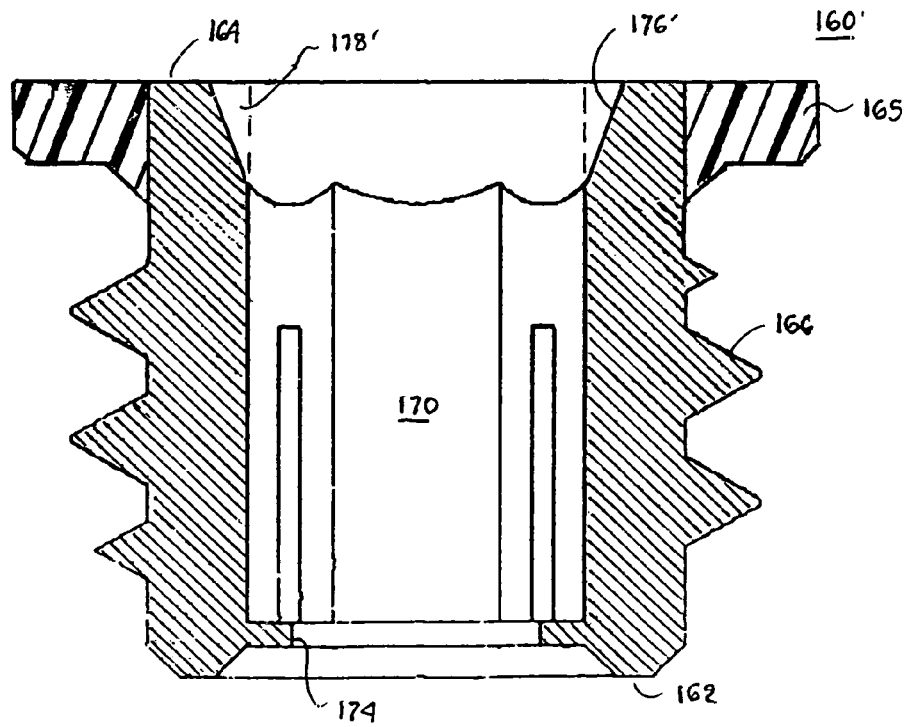
FIG. 13 is a side cross-section view taken along lines 13—13 of FIG. 12 of the setscrew illustrated in FIG. 12.

A further setscrew 160' that can be substituted for the setscrew 160 in any of the embodiments of the invention is depicted in FIGS. 12 and 13. In this embodiment of this aspect of the invention, the setscrew socket end 164 is enlarged in diameter by a ring 165 molded around the setscrew socket end 164.

Further embodiments of a ring-shaped retainer are illustrated in FIGS. 5–8 and 16–19, wherein the connector assemblies 240 and 242 each comprises a connector block 150, a setscrew 160, 160', a penetrable grommet 180, and a ring-shaped retainer formed in the shape of a retainer cap 250, 250', 250". As in the embodiment of FIGS. 1–3, the tubular grommet aperture 136 having a cylindrical grommet aperture sidewall 137 extends from side 130 into the header body 106 transverse to the axis of header connector bore 114. In this embodiment, an annular retention groove 234, 234' is formed around the grommet aperture 136 whereby a ring 236 of the thermoplastic material of the header body 110 is provided between the annular retention groove 234, 234' and the grommet aperture sidewall 137.

The retainer cap 250, 250', 250" is preferably formed of metal, e.g., stainless steel, having an annular cap end wall 252 surrounding a central cap opening 256 and a retainer cap sidewall 254 at the outer periphery of the annular cap end wall 252. The annular cap end wall 252 and the retainer cap sidewall 254 are preferably relatively thin.

Figures 6, 7:
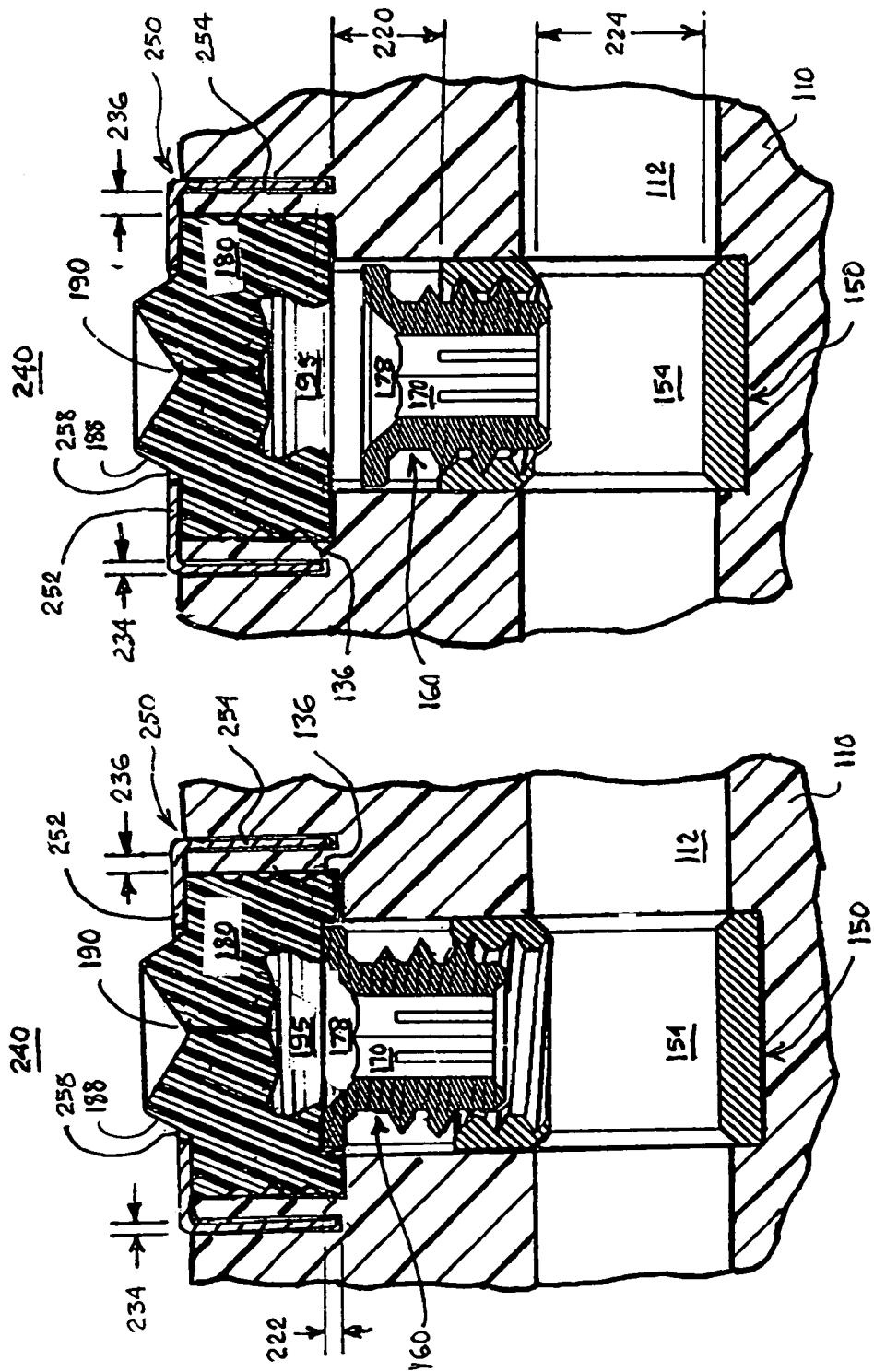
FIG. 6 is a cross-section view taken along lines 6—6 of FIG. 5 illustrating the retainer cap, the penetrable grommet within the grommet aperture, and the connector block within the connector header body with the setscrew in a partially advanced position to bear against a lead connector element within the connector bore.
FIG. 7 is a cross-section view taken along lines 6—6 of FIG. 5 illustrating the retainer cap, the penetrable grommet within the grommet aperture, and the connector block within the connector header body with the setscrew in the retracted position to frictionally engage against the grommet inner end wall to inhibit unintentional rotation and movement to the advanced position of FIG. 3.

In assembly, the connector block 150 is fitted into the connector block cavity, the setscrew 160, 160' is threaded into the threaded bore 152, and the penetrable grommet 180 is inserted into the grommet aperture 136. The retainer cap sidewall 254 is inserted into the annular retention groove 234, 234' so that the annular cap end wall 252 fits against the annular portion 185 of the grommet outer end wall 184, and the circular, outwardly projecting portion 188 projects outward through the central cap opening 256. The advanced and retracted positions of the setscrew 160 with respect to the connector block 150 and the penetrable grommet 180 are depicted in FIGS. 6 and 7, and all of the above-described aspects of the invention can be realized in this embodiment of the retainer.

The opaque, metallic, annular portion 185 of the grommet outer end wall 184 visually highlights the location of the pre-formed slit 190 and guides insertion of the setscrew hex wrench therethrough. Advantageously, the retainer cap sidewall 254 fitted into the cylindrical retention groove 234, 234' reinforces the material of the connector header body 110 that otherwise becomes dimensionally less stable due to chronic immersion in body fluids and/or pressure applied by the penetrable grommet 180 against the grommet aperture side wall 137. In particular, the ring 236 of the thermoplastic material of the header body 110 and the grommet aperture sidewall 137 are stabilized by the rigid metallic retainer cap sidewall 254 fitted into the cylindrical retention groove 234, 234'. The retainer cap sidewall 254 is preferably a continuous sidewall although it can comprise a plurality of spaced apart sidewall segments.

The width of the cylindrical retention groove 234, 234' and the thickness of the rigid metallic retainer cap sidewall 254 can be specified to provide an interference fit requiring a specified force to insert and seat the retainer cap sidewall 254 into the cylindrical retention groove 234, 234'. In some embodiments, at least one retention element is provided to enhance the holding force of the retainer cap sidewall 254 within the cylindrical retention groove 234, 234' during implantation and over prolonged chronic implantation in body fluids.

For example, the retainer cap 250' illustrated in FIG. 8 incorporates a plurality of stamped retention flanges 260, 262, 264, 266, 268, etc., formed through the retainer cap sidewall 254 to extend inward or outward and distributed around the circumference of the retainer cap sidewall 254. The outward extending edges of the retention flanges 260, 262, 264, 266, 268, etc., bite into a sidewall of the retention groove 234, 234' and resist dislodgement of the retainer cap 250'. The number and shape of the retention flanges can be varied from those shown in FIG. 8.

It will also be appreciated that the retention flanges 260, 262, 264, 266, 268, etc., can be employed as enhancements for promoting adhesion with the header body upon application of thermal energy to the thermoplastic material of the header body contacting the enhancements. Ultrasonic welding techniques of the type described in the above-referenced Publication No. 2003/0040780 can be employed to effect the thermal welding, particularly where the retention flanges 260, 262, 264, 266, 268, etc., bite into a sidewall of the retention groove 234, 234'. The ultrasonic energy applied against the outer annular side 252 by the shaped head of an ultrasonic generator concentrates where the edges of the retention flanges 260, 262, 264, 266, 268, etc., contact the thermoplastic material of the header body 110. Localized melting of the thermoplastic material occurs along the edges that enhances adhesion of the retention flanges 260, 262, 264, 266, 268, etc., with the sidewall of the retention groove 234 upon cooling.

Further enhancements of the interface between the retention groove 234 and the rigid metallic retainer cap sidewall 254 are depicted in FIGS. 16–19 that can be employed with or without the depicted retention flanges 260, 262, 264, 266, 268, etc. In this aspect of the invention, the enhancements comprise at least one aperture through the cap sidewall 254 into which thermoplastic material flows upon melting through application of thermal energy and solidifies upon cooling of the thermoplastic material. In one approach to forming such apertures, triangular notches 270, 272, 274, 276, etc., having key slots extending to the free edge of the cap sidewall 254 are formed in the retainer cap sidewall 254 distributed around the circumference thereof. A corresponding number of keys 284 are formed in the groove 234' as shown in FIGS. 17 and 18.

During assembly, the cap sidewall 254 is inserted into the groove 234' surrounding the grommet aperture 136 so that each key 284 fits into a notch, e.g., notch 274, as shown in FIG. 17, and points of contact are achieved as shown in FIG. 18. Force and ultrasonic energy are applied against the outer annular side 252 of the retainer cap 250" as shown in FIG. 18. Each key 284 heats until it melts as it is vibrated by the ultrasonic energy transmitted to the points of contact. The melted key material fills the triangular notch 274 and interlocks therewith upon cooling as shown in FIG. 19. It will be understood that the notches 270, 272, 274, 276, etc., can take other shapes, e.g., circular rather than triangular shapes.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical operation of mechanical instruments that are not disclosed and are not necessary to the practice of the present invention.

In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

The invention claimed is:

1. An implantable medical device having a connector header adapted to be coupled through the use of a tool to an electrical lead connector element of an elongated electrical medical lead, wherein:
   the connector header is formed of a dielectric header body having at least one header connector bore and a header grommet aperture having a grommet aperture sidewall;
   a connector block is disposed within the connector header having a threaded bore aligned with the header grommet aperture and a connector block bore aligned with the header connector bore adapted to receive the lead connector element when a proximal connector assembly of the elongated electrical medical lead is received in the header connector bore;
   a setscrew is threaded into the threaded bore having a setscrew socket disposed to be engaged by the tool to enable rotation of the setscrew within the threaded bore to tighten the setscrew against or to loosen the setscrew from a lead connector element received in the header connector bore; and
   a penetrable grommet is disposed within the header grommet aperture, the penetrable grommet comprising a generally cylindrical elastomer body having a grommet central axis and including a pre-formed resealable slit extending between opposed grommet inner and outer end walls enabling passage of the tool therethrough into the setscrew socket for rotating the setscrew and sealing of the pre-formed slit upon withdrawal of the tool, the elastomer body comprising a compound of silicone rubber filled with an additive decreasing the tendency of slit healing over time and facilitating passage of the tool therethrough into the setscrew socket for rotating the setscrew and sealing of the slit upon withdrawal of the tool.

2. The implantable medical device of claim 1, wherein the elastomer body of the penetrable grommet is formed of a compound of silicone rubber compounded with titanium dioxide in a concentration of up to about two percent by weight.

3. The implantable medical device of claim 2, wherein:
the header body is formed of a dielectric material of a first color, and
the additive colors the compound in a color contrasting from the first color providing a visible target for precisely aligning and inserting the tool through the central bore and the slit into operative engagement with the setscrew.

4. The implantable medical device of claim 1, wherein:
the header body is formed of a dielectric material of a first color, and
the additive colors the compound in a color contrasting from the first color providing a visible target for precisely aligning and inserting the tool through the central bore and the pre-formed slit into operative engagement with the setscrew.

5. The implantable medical device of claim 1, wherein the generally cylindrical elastomer body of the penetrable grommet includes a grommet sidewall extending between the opposed inner and outer end walls, the grommet sidewall formed having an irregular surface comprising a plurality of peaks and valleys that maintains fluid sealing contact with the cylindrical sidewall of the tubular header grommet aperture without adhesive therebetween.

6. The implantable medical device of claim 5, wherein the grommet aperture has a nominal inner diameter and the grommet sidewall is formed having a nominal peak-to-peak outer diameter exceeding the nominal inner diameter of the sidewall to provide a low pressure interference fit upon insertion of the penetrable grommet into the header grommet aperture, whereby a low, uniform, interference pressure is attained over a wide tolerance upon assembly that is maintained even if the inner diameter of the cylindrical sidewall of the tubular header grommet aperture changes over extended time periods.

7. The implantable medical device of claim 5, wherein the grommet aperture has a nominal inner diameter and the grommet sidewall is formed having a plurality of sealing rings having nominal sealing ring outer diameters exceeding the nominal inner diameter of the sidewall to provide a low pressure interference fit upon insertion of the penetrable grommet into the header grommet aperture, whereby a low, uniform, interference pressure is attained over a wide tolerance upon assembly that is maintained even if the inner diameter of the cylindrical sidewall of the tubular header grommet aperture changes over extended time periods.

8. The implantable medical device of claim 1, wherein a yield space is provided between the inner end wall of the grommet and the setscrew socket to accommodate the elastomer body of the grommet that is pushed inward by the tool advanced through the pre-formed slit.

9. The implantable medical device of claim 8, wherein the yield space is provided at least in part by a recess extending into the inner end wall of the penetrable grommet.

10. An implantable medical device having a connector header adapted to be coupled through the use of a tool to an electrical lead connector element of an elongated electrical medical lead, wherein:
the connector header is formed of a header body formed of a material of a first color and having at least one header connector bore and a header grommet aperture having a grommet aperture sidewall;
a connector block is disposed within the connector header having a threaded bore aligned with the header grommet aperture and a connector block bore aligned with the header connector bore adapted to receive the lead connector element when a proximal connector assembly of the elongated electrical medical lead is received in the header connector bore;
a setscrew is threaded into the threaded bore having a setscrew socket disposed to be engaged by the tool to enable rotation of the setscrew within the threaded bore to tighten the setscrew against or to loosen the setscrew from a lead connector element received in the header connector bore; and
a penetrable grommet is disposed within the header grommet aperture, the penetrable grommet comprising a generally cylindrical elastomer body having a grommet central axis and including a resealable pre-formed slit extending between opposed inner and outer end walls enabling passage of the tool therethrough into the setscrew socket for rotating the setscrew and sealing of the pre-formed slit upon withdrawal of the tool, the elastomer body comprising a compound of silicone rubber filled with an additive that colors the compound in a color contrasting from the first color providing a visible target for precisely aligning and inserting the tool through the central bore and the pre-formed slit into operative engagement with the setscrew.

11. The implantable medical device of claim 10, wherein the penetrable grommet disposed within the header grommet aperture is formed of a compound of silicone rubber compounded with titanium dioxide in a concentration of up to about two percent by weight.

12. The implantable medical device of claim 10, wherein the generally cylindrical elastomer body of the penetrable grommet includes a grommet sidewall extending between the opposed inner and outer end walls, the grommet sidewall formed having an irregular surface comprising a plurality of peaks and valleys that maintains fluid sealing contact with the cylindrical sidewall of the tubular header grommet aperture without adhesive therebetween.

13. The implantable medical device of claim 12, wherein the grommet aperture has a nominal inner diameter and the grommet sidewall is formed having a nominal peak-to-peak outer diameter exceeding the nominal inner diameter of the sidewall to provide a low pressure interference fit upon insertion of the penetrable grommet into the header grommet aperture, whereby a low, uniform, interference pressure is attained over a wide tolerance upon assembly that is maintained even if the inner diameter of the cylindrical sidewall of the tubular header grommet aperture changes over extended time periods.

14. The implantable medical device of claim 12, wherein the grommet aperture has a nominal inner diameter and the grommet sidewall is formed having a plurality of sealing rings having nominal sealing ring outer diameters exceeding the nominal inner diameter of the sidewall to provide a low pressure interference fit upon insertion of the penetrable grommet into the header grommet aperture, whereby a low, uniform, interference pressure is attained over a wide tolerance upon assembly that is maintained even if the inner diameter of the cylindrical sidewall of the tubular header grommet aperture changes over extended time periods.

15. The implantable medical device of claim 10, wherein a yield space is provided between the inner end wall of the grommet and the setscrew socket to accommodate the elastomer body of the grommet that is pushed inward by the tool advanced through the slit.

16. The implantable medical device of claim 15, wherein the yield space is provided at least in part by a recess extending into the inner end wall of the penetrable grommet.

17. An implantable medical device having a connector header adapted to be coupled through the use of a tool to an electrical lead connector element of an elongated electrical medical lead, wherein:
the connector header is formed of a dielectric header body having at least one header connector bore and a header grommet aperture having a grommet aperture sidewall;
a connector block is disposed within the connector header having a threaded bore aligned with the header grommet aperture and a connector block bore aligned with the header connector bore adapted to receive a lead connector element when a proximal connector assembly of the elongated electrical medical lead is received in the header connector bore;
a setscrew is threaded into the threaded bore having a setscrew socket disposed to be engaged by the tool to enable rotation of the setscrew within the threaded bore to tighten the setscrew against or to loosen the setscrew from a lead connector element received in the header connector bore;
a penetrable grommet is disposed within the header grommet aperture, the penetrable grommet comprising a generally cylindrical elastomer body having a grommet central axis and including a resealable pre-formed slit extending between opposed grommet inner and outer end walls enabling passage of the tool therethrough into the setscrew socket for rotating the setscrew and sealing of the pre-formed slit upon withdrawal of the tool; and
the generally cylindrical elastomer body of the penetrable grommet includes a grommet sidewall extending between the opposed grommet inner and outer end walls, the grommet sidewall formed having an irregular surface comprising a plurality of peaks and valleys that maintains fluid sealing contact with the cylindrical sidewall of the tubular header grommet aperture without adhesive therebetween.

18. The implantable medical device of claim 17, wherein the grommet aperture has a nominal inner diameter and the grommet sidewall is formed having a nominal peak-to-peak outer diameter exceeding the nominal inner diameter of the sidewall to provide a low pressure interference fit upon insertion of the penetrable grommet into the header grommet aperture, whereby a low, uniform, interference pressure is attained over a wide tolerance upon assembly that is maintained even if the inner diameter of the cylindrical sidewall of the tubular header grommet aperture changes over extended time periods.

19. The implantable medical device of claim 18, wherein a yield space is provided between the inner end wall of the grommet and the setscrew socket to accommodate the elastomer body of the grommet that is pushed inward by the tool advanced through the pre-formed slit.

20. The implantable medical device of claim 19, wherein the yield space is provided at least in part by a recess extending into the inner end wall of the penetrable grommet.

21. The implantable medical device of claim 17, wherein the grommet aperture has a nominal inner diameter and the grommet sidewall is formed having a plurality of sealing rings having nominal sealing ring outer diameters exceeding the nominal inner diameter of the sidewall to provide a low pressure interference fit upon insertion of the penetrable grommet into the header grommet aperture, whereby a low, uniform, interference pressure is attained over a wide tolerance upon assembly that is maintained even if the inner diameter of the cylindrical sidewall of the tubular header grommet aperture changes over extended time periods.

22. The implantable medical device of claim 21, wherein a yield space is provided between the inner end wall of the grommet and the setscrew socket to accommodate the elastomer body of the grommet that is pushed inward by the tool advanced through the pre-formed slit.

23. The implantable medical device of claim 22, wherein the yield space is provided at least in part by a recess extending into the inner end wall of the penetrable grommet.

* * * * *